US012806053B2

(12) United States Patent
Liu et al.

(10) Patent No.: US 12,806,053 B2
(45) Date of Patent: Nov. 24, 2026

(54) SHEATH CORE ASSEMBLY AND DELIVERY INSTRUMENT

(71) Applicant: Lifetech Scientific (Shenzhen) Co. Ltd., Shenzhen (CN)

(72) Inventors: Kui Liu, Shenzhen (CN); Benhao Xiao, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 247 days.

(21) Appl. No.: 18/724,252

(22) PCT Filed: Dec. 15, 2022

(86) PCT No.: PCT/CN2022/139209

§ 371 (c)(1),
(2) Date: Jun. 26, 2024

(87) PCT Pub. No.: WO2023/125031

PCT Pub. Date: Jul. 6, 2023

(65) Prior Publication Data

US 2025/0057674 A1 Feb. 20, 2025

(30) Foreign Application Priority Data

Dec. 31, 2021 (CN) ......................... 202111675505.4
Dec. 31, 2021 (CN) ......................... 202111678807.7
Dec. 31, 2021 (CN) ......................... 202123451901.7

(51) Int. Cl.
*A61F 2/966* (2013.01)

(52) U.S. Cl.
CPC ...... *A61F 2/966* (2013.01); *A61F 2002/9665* (2013.01); *A61F 2230/0013* (2013.01)

(58) Field of Classification Search
CPC .. A61F 2/966; A61F 2/962; A61F 2002/9623; A61F 2002/9665; A61F 2230/0013
See application file for complete search history.

(56) References Cited

U.S. PATENT DOCUMENTS 7,451,765 B2 * 11/2008 Adler ............... A61B 17/12172 128/207.14
8,414,640 B2 4/2013 Schmitt et al.
(Continued)

FOREIGN PATENT DOCUMENTS

CN 107961098 A 4/2018
CN 208823066 U 5/2019
(Continued)

OTHER PUBLICATIONS

First Office action in corresponding China Appl. No. 202111675505.4.
(Continued)

*Primary Examiner* — Phong Son H Dang
(74) *Attorney, Agent, or Firm* — Raymond Sun

(57) ABSTRACT

A sheath core assembly (100) and a delivery system are provided. The sheath core assembly (100) includes a sheath core (10) and a U-shaped anchor (20). The U-shaped anchor (20) includes an anchor body (21) and a stent fixing rod (22). The anchor body (21) surrounds the sheath core (10) and relatively fixed to the sheath core (10). The anchor body (21) includes a distal face (21*a*) and a proximal face (21*b*) which are opposite to each other, and an outer peripheral face (21*c*) surrounded between the distal face (21*a*) and the proximal face (21*b*). The distal face (21*a*) is larger than the proximal face (21*b*), and edge profiles of the distal face (21*a*) and the proximal face (21*b*) are arc-shaped. The outer peripheral face (21*c*) is an arc face having a smooth transition from the distal face (21*a*) to the proximal face (21*b*). A welding groove (24) is recessed in the outer peripheral face (21*c*) near a proximal end of the anchor body (21). A proximal end of the stent fixing rod (22) is fixedly connected to the distal face (21*a*) of the anchor body (21). In the sheath core assembly, an outer periphery of the anchor body is arranged as an arc-shaped transition face, and a welding groove is
(Continued)

recessed in the arc-shaped transition face, whereby a distal end of the anchor body has no step, thus solving the problem of difficulty in pushing and withdrawing due to the existence of steps in a welding zone.

18 Claims, 9 Drawing Sheets

(56) References Cited

U.S. PATENT DOCUMENTS

| | | | | | |
|---|---|---|---|---|---|
| 11,259,945 | B2 * | 3/2022 | Berra | A61F 2/966 | |
| 11,376,145 | B2 * | 7/2022 | Arbefeuille | A61F 2/9662 | |
| 11,547,584 | B2 * | 1/2023 | Lostetter | A61F 2/07 | |
| 2008/0262590 | A1 * | 10/2008 | Murray | A61F 2/95 | 623/1.11 |
| 2008/0264102 | A1 * | 10/2008 | Berra | A61F 2/966 | 623/1.15 |
| 2009/0254165 | A1 * | 10/2009 | Tabor | A61F 2/2412 | 623/1.11 |
| 2010/0268317 | A1 | 10/2010 | Stiger et al. | | |
| 2013/0274859 | A1 * | 10/2013 | Argentine | A61F 2/95 | 623/1.11 |
| 2013/0274860 | A1 * | 10/2013 | Argentine | A61F 2/9517 | 623/1.11 |
| 2014/0358215 | A1 | 12/2014 | Baylis | | |
| 2016/0270901 | A1 * | 9/2016 | Berra | A61F 2/89 | |
| 2017/0281382 | A1 * | 10/2017 | Lostetter | A61F 2/07 | |
| 2019/0351182 | A1 | 11/2019 | Chou et al. | | |
| 2019/0374358 | A1 | 12/2019 | Nageswaran | | |
| 2022/0117764 | A1 * | 4/2022 | Jiang | A61F 2/966 | |
| 2023/0225864 | A1 * | 7/2023 | Pham | A61F 2/2418 | 623/1.11 |

FOREIGN PATENT DOCUMENTS

| | | | |
|---|---|---|---|
| CN | 111359077 | A | 7/2020 |
| CN | 211433527 | U | 9/2020 |
| CN | 212679351 | U | 3/2021 |
| CN | 216676051 | U | 6/2022 |
| EP | 2742879 | A2 | 6/2014 |
| WO | WO2020011132 | A1 | 1/2020 |
| WO | WO 2021/226418 | A1 | 11/2021 |

OTHER PUBLICATIONS

First Office action in corresponding China Appl. No. 202111678807.7.

Search Report dated Mar. 26, 2025 for corresponding European Application No. EP 22914286.4.

International Search Report dated Mar. 14, 2023 for corresponding PCT Application No. PCT/CN2022/139209.

CN 211433527 U (Shanghai Microport Cardioflow Medtech Co., Ltd.) Sep. 8, 2020 (Sep. 8, 2020) description, paragraphs 43-51, figures 1-4b.

WO 2020011132 A1 (Lifetech Scient Shenzhen Co.) Jan. 16, 2020 (Jan. 16, 2020) description, p. 6 line 2 to p. 8 line 21, figures 1-5.

CN 212679351 U (Venus Medtech (Hangzhou) Inc.) Mar. 12, 2021 (Mar. 12, 2021) description, paragraphs 111-118, and figures 6 and 7.

CN 216676051 U (Lifetech Scientific (Shenzhen) Co., Ltd.) Jun. 7, 2022 (Jun. 7, 2022) claims 1-10.

CN 111359077 A (Butler Biotechnology (Suzhou) Co., Ltd.) Jul. 3, 2020 (Jul. 3, 2020) entire document.

India office action dated Jun. 1, 2026 for Corresponding Application No. 202417057547.

Office action dated Apr. 28, 2026 in corresponding China application No. 202111675505.4.

Office action dated Apr. 30, 2026 in corresponding China application No. 202111678807.7.

* cited by examiner

SHEATH CORE ASSEMBLY AND DELIVERY INSTRUMENT

CROSS-REFERENCE TO RELATED APPLICATIONS

This application claims priorities of Chinese patent application No. 2021116788077 filed with the China National Intellectual Property Administration on Dec. 31, 2021 and entitled "Sheath Core Assembly and Delivery Instrument", Chinese patent application No. 2021234519017 filed with the China National Intellectual Property Administration on Dec. 31, 2021 and entitled "Sheath Core Assembly and Delivery Instrument", and Chinese patent application No. 2021116755054 filed with the China National Intellectual Property Administration on Dec. 31, 2021 and entitled "Sheath Core Assembly and Delivery Instrument", the entire contents of which are incorporated herein by reference.

TECHNICAL FIELD

The present invention relates to the technical field of interventional medical instruments, and more particularly to a sheath core assembly and a delivery system.

BACKGROUND ART

In recent years, interventional therapy for cardiovascular diseases has become a development trend. With the continuous development of interventional technology, the advantages of using a covered stent in the therapy of aortic aneurysm and arterial dissection have become increasingly prominent. The covered stent is an artificial blood vessel adapted to the size of blood vessels, which is mainly composed of a covered membrane and a metal wave coil supporting the covered membrane. The covered membrane is generally made of a polyester or e-PTFE membrane, and the metal wave coil is mainly woven by a nickel-titanium alloy wire. When the covered stent is delivered to a lesion site for therapy by using a delivery device, the stent is first compressed into a sheath of the delivery device, the blood vessel is punctured, and a track is established by using a guide wire to deliver the delivery device to a designated position of the lesion. Then the stent is released, and the stent is unfolded and attached to the aneurysm vascular wall. The stent covering isolates the blood flow from the lesion site, eliminates the impact of the blood flow on the aneurysm wall at the lesion site, and re-establishes a normal channel of blood circulation. Finally, the guide wire and the delivery device are withdrawn, thus realizing interventional therapy of aneurysm and arterial dissection.

The existing iliac artery bifurcation stent delivery device, as shown in FIG. 1, has a sheath core assembly composed of a tip 1, a bifurcation tube 2, a U-shaped anchor 3, and a sheath core 4. As shown in FIG. 2, the U-shaped anchor 3 is composed of a stent fixing rod 3-2 and a welding zone 3-1. The U-shaped anchor 3 is configured to hook a proximal end of a stent to allow for the post-release of the stent. The welding zone 3-1 of the U-shaped anchor 3 is a separate section of the stainless-steel tube. After the sheath core 4 is welded and fixed to the welding zone 3-1 of the U-shaped anchor 3, a circumferential step m is formed with the sheath core 4 at a distal end of the welding zone 3-1. As shown in FIG. 3, when a sheath core is withdrawn from a curved blood vessel a, the step m of the U-shaped anchor 3 may hook the stent to cause shifting of the stent or may hook a vascular wall and is thus difficult to withdraw.

The structure of the existing bifurcation tube 2 is shown in FIG. 4. The bifurcation tube 2 is configured to connect and fix the tip 1 to the sheath core 4. The bifurcation tube 2 has a welding zone 2-1 and a fixing zone 2-2. The two functional zones are arranged at different positions of the bifurcation tube 2, resulting in a large overall length L1 of the bifurcation tube. Also, since the bifurcation tube 2 is buried in the tip 1, a length L2 of a high-hardness zone of the tip 1 is large, thus reducing the compliance of the tip 1 and affecting the pushing and withdrawing of the punctured tissue of the sheath core 4 in the blood vessel. In addition, when the bifurcation tube 2 is used for injection molding of the tip 1, the fixing zone 2-2 of the bifurcation tube 2 will be deformed or even broken in an arrow direction due to the injection molding pressure (the pressure direction is as indicated by arrows in FIG. 4), which will reduce the connection strength and seriously lead to connection failure.

The U-shaped anchor 3 is composed of a stent fixing rod 3-2 and a welding zone 3-1. The U-shaped anchor 3 surrounds the sheath core 4, and the welding zone 3-1 is fixed to the sheath core 4. In addition, the bifurcation tube 2 also surrounds a distal end of the sheath core 4, and the tip wraps the distal end of the sheath core 4, while the sheath core 4 is usually a stainless-steel tube, which leads to high hardness and poor compliance of the distal end of the sheath core 4. As shown in FIG. 3, the sheath core cannot bend or recover in time to comply with the shape of the blood vessel a, and the blood vessel a conflicts with the sheath core to form a resistance zone a1, which will make it difficult to push or withdraw the sheath core.

SUMMARY OF THE INVENTION

Based on the above-mentioned problems, the present invention provides a sheath core assembly and a delivery system, aiming at solving at least one of the above-mentioned technical problems.

To achieve the above object, the present invention adopts a technical solution as follows.

The present invention provides a sheath core assembly, including a sheath core and a U-shaped anchor. The U-shaped anchor includes an anchor body and a stent fixing rod. The anchor body surrounds the sheath core and is relatively fixed to the sheath core. The anchor body includes a distal face and a proximal face which are opposite to each other, and an outer peripheral face surrounded between the distal face and the proximal face. The distal face is larger than the proximal face, and edge profiles of the distal face and the proximal face are arc-shaped. The outer peripheral face is an arc face having a smooth transition from the distal face to the proximal face. A proximal end of the stent fixing rod is fixedly connected to the distal face of the anchor body.

In one embodiment, the distal face and the proximal face have the same shape.

In one embodiment, both the distal face and the proximal face of the anchor body are round, whereby the anchor body is approximately conical.

In one embodiment, an accommodating groove cut from the distal face is recessed in the outer peripheral face near a distal end of the anchor body, and the accommodating groove is provided near the stent fixing rod, whereby a connecting arm of a stent hooked on the stent fixing rod is placed in the accommodating groove.

In one embodiment, both sides of the stent fixing rod are provided with the accommodating grooves, whereby the connecting arms connected to both sides of a hooking portion of the stent are accommodated in the accommodating grooves on both sides of the stent fixing rod respectively.

In one embodiment, both the distal face and the proximal face of the anchor body are elliptic, whereby the anchor body is approximately elliptically conical.

In one embodiment, there are two stent fixing rods, which are opposite to each other in a radial direction of the distal face.

In one embodiment, a welding groove is recessed in the outer peripheral face near the proximal end of the anchor body.

In one embodiment, multiple welding grooves are provided at intervals circumferentially along the outer peripheral face of the anchor body.

In one embodiment, the anchor body is axially provided with two symmetrical pulling wire holes, and the pulling wire holes are opposite to exhaust grooves on a tip in the sheath core assembly.

In one embodiment, the sheath core assembly further includes a connector surrounding a distal end of the sheath core and configured to connect the sheath core to the tip. A groove is recessed in an outer peripheral surface of the connector, and the connector is relatively fixed to the sheath core and the tip through the groove.

In one embodiment, the connector has a polygonal radial cross-section, whereby an outer peripheral face of the connector includes multiple surfaces, and the groove is recessed in the outer peripheral surface of the connector.

In one embodiment, the connector has a quadrilateral radial cross-section, whereby the outer peripheral face of the connector includes four surfaces, and the groove includes a first groove provided on the surface and cut from a distal face and a proximal face of the connector and/or includes a second groove recessed circumferentially along the outer peripheral face of the connector.

In one embodiment, the groove includes a third groove recessed circumferentially along the outer peripheral face of the connector, blocking portions are formed at a proximal side and a distal side of the third groove respectively and have quadrilateral radial cross-sections, and two opposite sides of the quadrilateral are straight lines while the other two opposite sides are arc lines, whereby two opposite faces of the blocking portion are arc faces, and the arc faces of the two blocking portions at the proximal side and the distal side are interlaced in azimuth.

In one embodiment, the sheath core includes a first tube body and a second tube body retained in the first tube body, a distal end of the second tube body extends out of a distal face of the first tube body, and the compliance of the second tube body is superior to that of the first tube body.

In one embodiment, the first tube body is a cylindrical tube, and the second tube body is a helical tube.

In one embodiment, the first tube body includes a first section surrounding the outside of the second tube body and a second section connected to a distal end of the first section, and the first section is provided with a notch.

In one embodiment, multiple notches are provided at intervals along an axial direction of the first section.

In one embodiment, the adjacent notches on the first section are provided at equal intervals from a proximal end of the first section to the distal end thereof.

In one embodiment, the adjacent notches on the first section are provided at gradually reducing intervals from a proximal end of the first section to the distal end thereof.

In one embodiment, the notch is a helical notch which extends helically along an axial direction of the first section.

In one embodiment, the adjacent helical notches on the first section are provided at gradually reducing intervals from a proximal end of the first section to the distal end thereof.

In one embodiment, the length between the nearest and farthest notches on the first section is 5-200 mm.

The present invention adopts another technical solution.

The present invention also provides a delivery instrument, including the sheath core assembly as described above.

The present invention adopts yet another technical solution.

The present invention provides a sheath core assembly, including a sheath core and a connector surrounding a distal end of the sheath core and configured to connect the sheath core to the tip. A groove is recessed in an outer peripheral surface of the connector, and the connector is relatively fixed to the sheath core and the tip through the groove.

In one embodiment, the connector has a polygonal radial cross-section, whereby an outer peripheral face of the connector includes multiple surfaces, and the groove is recessed in the outer peripheral surface of the connector.

In one embodiment, the connector has a quadrilateral radial cross-section, whereby the outer peripheral face of the connector includes four surfaces, and the groove includes a first groove provided on the surface and penetrating a distal face and a proximal face of the connector and/or includes a second groove recessed circumferentially along the outer peripheral face of the connector.

In one embodiment, the groove includes a third groove recessed circumferentially along the outer peripheral face of the connector, blocking portions are formed at a proximal side and a distal side of the third groove respectively and have quadrilateral radial cross-sections, and two opposite sides of the quadrilateral are straight lines while the other two opposite sides are arc lines, whereby two opposite faces of the blocking portion are arc faces, and the arc faces of the two blocking portions at the proximal side and the distal side are interlaced in azimuth.

In one embodiment, the sheath core includes a first tube body and a second tube body retained in the first tube body, a distal end of the second tube body extends out of a distal face of the first tube body, and the compliance of the second tube body is superior to that of the first tube body.

In one embodiment, the first tube body is a cylindrical tube, and the second tube body is a helical tube.

In one embodiment, the first tube body includes a first section sleeved outside the second tube body and a second section connected to a distal end of the first section, and the first section is provided with a notch.

In one embodiment, multiple notches are provided at intervals along an axial direction of the first section.

In one embodiment, the adjacent notches on the first section are provided at equal intervals from a proximal end of the first section to the distal end thereof.

In one embodiment, the adjacent notches on the first section are provided at gradually reducing intervals from a proximal end of the first section to the distal end thereof.

In one embodiment, the notch is a helical notch which extends helically along an axial direction of the first section.

In one embodiment, the adjacent helical notches on the first section are provided at gradually reducing intervals from a proximal end of the first section to the distal end thereof.

In one embodiment, a length between the nearest and farthest notches on the first section is 5-200 mm.

The present invention adopts another technical solution.

The present invention also provides a delivery instrument, including the sheath core assembly as described above.

The present invention adopts yet another technical solution.

The present invention provides a sheath core assembly, including a sheath core. The sheath core includes a first tube body and a second tube body retained in the first tube body. A distal end of the second tube body extends out of a distal face of the first tube body. The compliance of the second tube body is superior to that of the first tube body.

In one embodiment, the first tube body is a cylindrical tube, and the second tube body is a helical tube.

In one embodiment, the first tube body includes a first section surrounding the outside of the second tube body and a second section connected to a distal end of the first section, and the first section is provided with a notch.

In one embodiment, multiple notches are provided at intervals along an axial direction of the first section.

In one embodiment, the adjacent notches on the first section are provided at equal intervals from a proximal end of the first section to the distal end thereof.

In one embodiment, the adjacent notches on the first section are provided at gradually reducing intervals from a proximal end of the first section to the distal end thereof.

In one embodiment, the notch is a helical notch which extends helically along an axial direction of the first section.

In one embodiment, the adjacent helical notches on the first section are provided at equal or gradually reducing intervals from a proximal end of the first section to the distal end thereof.

In one embodiment, the length between the nearest and farthest notches on the first section is 5-200 mm.

The present invention adopts another technical solution.

The present invention also provides a delivery instrument, including the sheath core assembly as described above.

The present invention provides a sheath core assembly and a delivery instrument including the sheath core assembly. An outer periphery of an anchor body is arranged as an arc-shaped transition face, and a welding groove is recessed in the arc-shaped transition face, whereby a distal end of the anchor body has no step, thus solving the problem of difficulty in pushing and withdrawing due to steps in a welding zone, and greatly improving the smoothness of withdrawal of a delivery device in blood vessels, especially curved blood vessels. In addition, built-in welding spots avoid damage to the blood vessels by surface unevenness caused by welding, thus further improving the smoothness.

The present invention provides a sheath core assembly and a delivery instrument including the sheath core assembly. By designing a welding zone and a circumferential fixing zone of a connector in the same groove, the overall length of the connector is obviously smaller than the length of the existing bifurcation tube. By reducing the overall length, after the connector is buried in a tip, the length of a high-hardness zone of the tip is smaller, and the compliance is better. At the same time, the overall structure of the connector is more stable, and the connector will not be deformed during injection molding of the tip and is more reliably connected to the tip, thus solving the problems of difficulty in pushing and withdrawing and the fracture failure caused by the existing bifurcation tube.

The present invention provides a sheath core assembly and a delivery instrument including the sheath core assembly. A sheath core 10 is designed by combining a helical tube and a stainless-steel tube. The stainless-steel tube wraps an outer wall of the helical tube. The sheath core adopts the structure that the helical tube is located at a distal end while the stainless-steel tube is located at a proximal end. A notch is provided at a distal end of the stainless-steel tube, and the distal end is a closed section for being welded and fixed to the helical tube and sealing the notch. The notch achieves a flexible even transition between the helical tube and the stainless-steel tube, ensures the flexibility of the distal end of the sheath core 10 and the rigidity of the proximal end, ensures that a main body of the sheath core 10 has sufficient pushing property, and solves the problem of difficulty in pushing and withdrawing caused by the poor compliance of the distal end of the existing sheath core.

DETAILED DESCRIPTION OF THE INVENTION

Figure 1:
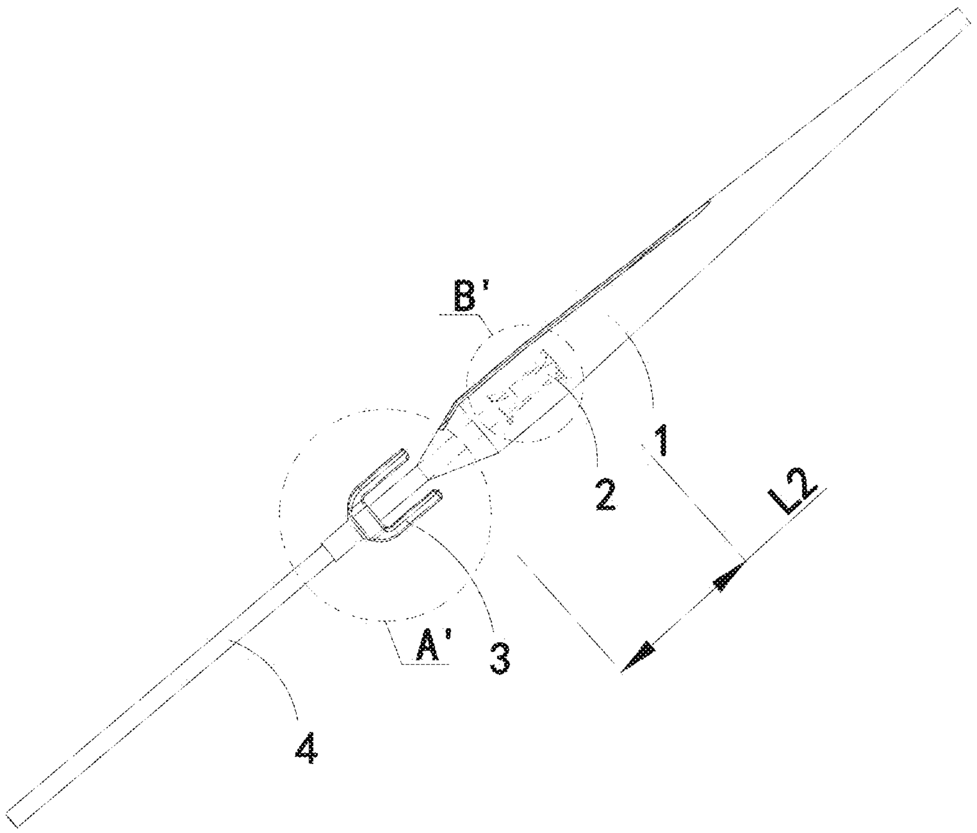
FIG. 1 is a schematic partial view of an existing sheath core assembly.

In order that the objects, technical solutions, and advantages of the present invention will become more apparent, exemplary implementations of the present disclosure will be described in detail below with reference to the accompanying drawings. While the drawings show exemplary implementations of the present disclosure, it should be understood that the present disclosure may be embodied in various forms and should not be limited by the implementations set forth herein. Rather, these implementations are provided so that the present disclosure will be thoroughly understood, and the scope of the present disclosure will be fully conveyed to those skilled in the art.

It should be understood that the terms used herein are for the purpose of describing particular example implementations only and are not intended to be limiting. As used herein, the singular forms “a/an”, “one”, and “the” are intended to include the plural forms as well, unless the context clearly indicates otherwise. The terms “comprising”, “including”, “containing”, and “having” are inclusive and therefore specify the presence of stated features, steps, operations, elements, and/or components, but do not preclude the presence or addition of one or more other features, steps, operations, elements, components, and/or combinations thereof. The method steps, processes, and operations described herein are not to be construed as necessarily requiring to be performed in the particular order described or illustrated, unless an order of performance is explicitly stated. It should also be understood that additional or alternative steps may be used.

Although the terms first, second, third, and the like may be used herein to describe various elements, components, regions, layers, and/or sections, these elements, components, regions, layers, and/or sections should not be limited by these terms. These terms may be used only to distinguish one element, component, region, layer, or section from another region, layer, or section. The use of terms such as “first”, “second”, and other numerical terms herein does not imply a sequence or order unless the context clearly dictates otherwise. Therefore, a first element, component, region, layer, or section discussed below may be referred to as a second element, component, region, layer, or section without departing from the teachings of example implementations.

For ease of description, spatially relative terms, such as “inner”, “outer”, “inside”, “outside”, “underneath”, “below”, “over”, and “above”, may be used herein to describe the relationship between one element or feature and another element or feature as illustrated in the figures. Such spatially relative terms are intended to encompass different orientations of a device in use or operation in addition to the orientations depicted in the figures. For example, if the device in the figures is turned over, elements described as “underneath” or “below” other elements or features would then be oriented “over” or “above” the other elements or features. Therefore, the example term “below” may include orientations: above and below. The device may be otherwise oriented (rotated by 90 degrees or in other directions) and is interpreted accordingly by spatially relative descriptors used herein.

It should be additionally noted that in the field of interventional medical instruments, an end of a medical instrument implanted in a human or animal body or a delivery system for delivering the medical instrument, which is closer to an operator, is generally referred to as a “proximal end”, an end which is further away from the operator is referred to as a “distal end”, and the “proximal end” and “distal end” of any component of the medical instrument or the delivery system are defined in accordance with this principle. An “axial direction” generally refers to a lengthwise direction of the medical instrument when being delivered, and a “radial direction” generally refers to a direction of the medical instrument perpendicular to the “axial direction” thereof, and the “axial direction” and “radial direction” of any component of the medical instrument are defined in accordance with this principle.

Embodiment 1

Figure 7:
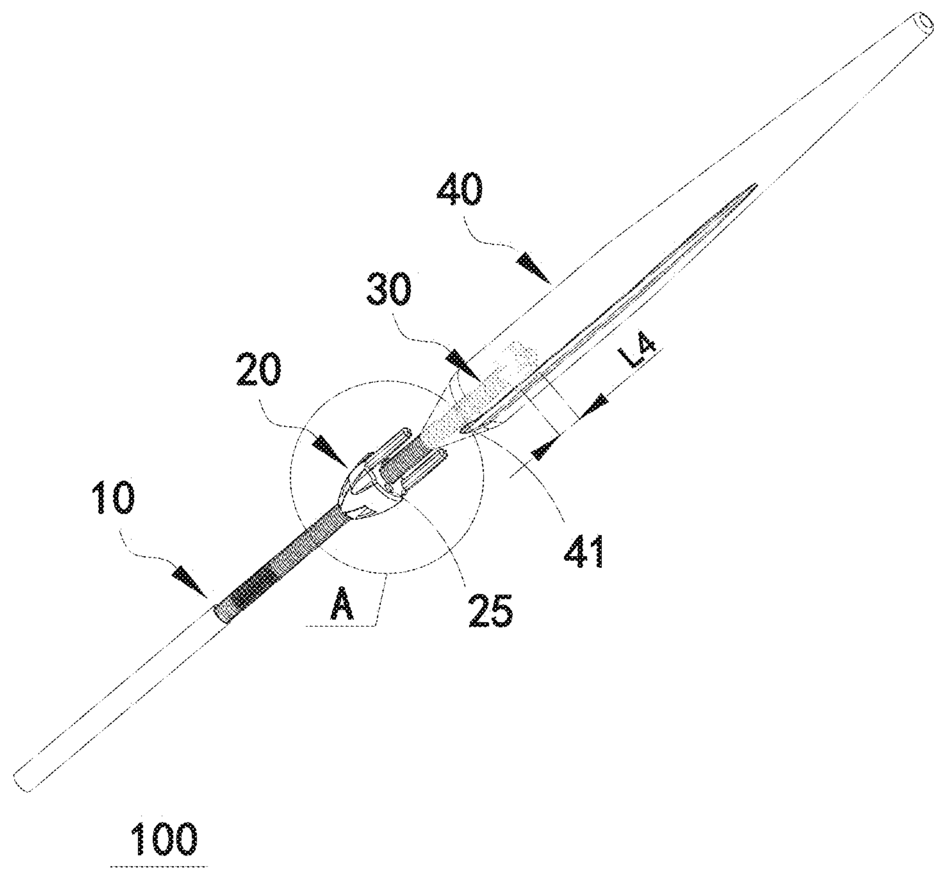
FIG. 7 is a schematic view depicting a structure of a sheath core assembly according to the present invention.

Referring to FIG. 7, in view of the problem that a circumferential step of a U-shaped anchor in an existing delivery device hooks a stent to cause shifting of the stent, or hooks a vascular wall and is thus difficult to withdraw, the present invention exemplarily provides a sheath core assembly 100 such that a delivery device including the sheath core assembly 100 of this embodiment may be smoothly pushed and withdrawn in a blood vessel.

Specifically, referring to FIG. 7, the sheath core assembly 100 of this embodiment includes a sheath core 10 and a U-shaped anchor 20 surrounding the sheath core 10 and relatively fixed to the sheath core 10. In addition, the sheath core assembly 100 may also include a tip 40 wrapping a distal end of the sheath core 10. The structure of the sheath core 10 in this embodiment may refer to the prior art. For example, the sheath core may be a stainless-steel tube. Preferably, a novel sheath core structure may also be provided. A detailed implementation of the novel sheath core structure may refer to the following Embodiment 3. The structure of the U-shaped anchor 20 in the sheath core assembly 100 is mainly described in detail in this embodiment.

Figure 8:
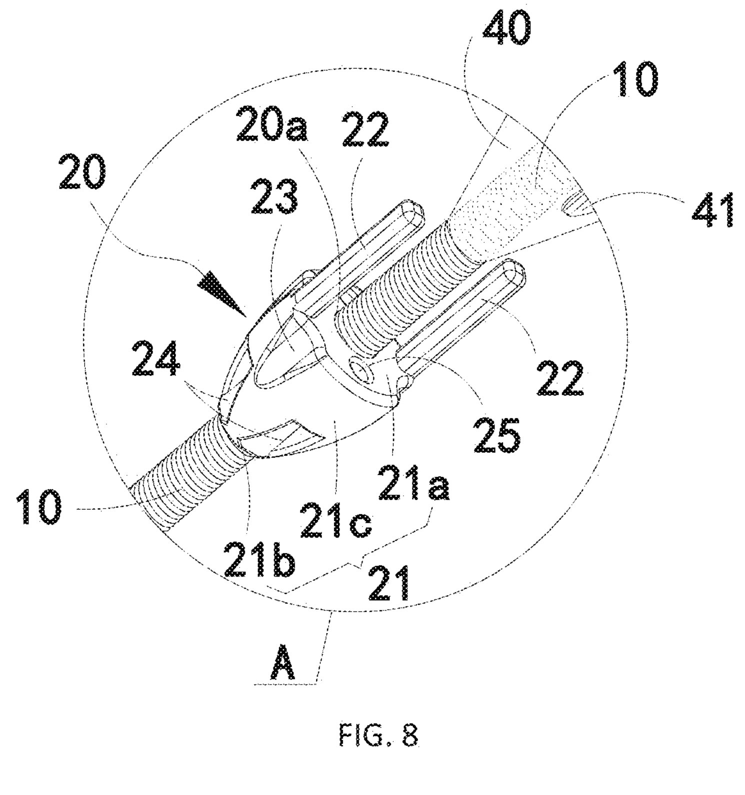
FIG. 8 is a schematic enlarged view of part A in FIG. 7.

As shown in FIG. 7 and FIG. 8, the U-shaped anchor 20 of this embodiment is different from the prior art in that the U-shaped anchor includes an anchor body 21 and a stent fixing rod 22. The anchor body 21 is axially provided with a via 20*a*. The anchor body 21 surrounds the sheath core 10 and is fixed relative to the sheath core 10 through the via 20*a*. The anchor body 21 includes a distal face 21*a* and a proximal face 21*b* which are opposite to each other, and an outer peripheral face 21*c* between the distal face 21*a* and the proximal face 21*b*. The distal face 21*a* is larger than the proximal face 21*b*, and edge profiles of the distal face 21*a* and the proximal face 21*b* are arc-shaped, whereby the outer peripheral face 21*c* is an arc face having a smooth transition from the distal face 21*a* to the proximal face 21*b*. A proximal end of the anchor body 21 of this embodiment has no step. Preferably, the distal face 21*a* and the proximal face 21*b* have the same shape in order to ensure the smooth transition of the outer peripheral face. With this arrangement, the outer peripheral face 21*c* formed by the distal face 21*a* and the proximal face 21*b* is free of edges and corners, thus ensuring smoothness for pushing and withdrawing.

A proximal end of the stent fixing rod 22 is fixedly connected to the distal face 21*a* of the anchor body 21. The stent fixing rod 22 is configured to hook a bare wave coil of a stent. After a wire is fixed to the U-shaped anchor 20, the stent may be brought into a sheath together to complete the assembly. In addition, the U-shaped anchor 20 also functions to release the stent.

Referring to FIG. 8, as an implementation of the anchor body 21 of this embodiment, both the distal face 21*a* and the proximal face 21*b* of the anchor body 21 are round, whereby the anchor body 21 is approximately conical, which means that the proximal face 21*b* of the anchor body 21 is as close as possible to an outer periphery of the sheath core 10 to which the anchor body is relatively fixed, whereby the proximal end of the anchor body 21 has no step. Preferably, the edge of a joint between the distal face 21*a* and the outer peripheral face 21*c* of the anchor body 21 is rounded to improve smoothness.

With continued reference to FIG. 8, when the anchor body 21 is approximately conical, an accommodating groove 23 extending through the distal face 21*a* is recessed in the outer peripheral face 21*c* near a distal end of the anchor body 21 preferably. The accommodating groove 23 is provided near the stent fixing rod 22, whereby a connecting arm of a stent hooked on the stent fixing rod 22 is placed in the accommodating groove 23. Since the space between an outer wall of the U-shaped anchor 20 and an inner wall of a sheath is limited, the accommodating groove 23 serves to enlarge the accommodating space between the sheath and the U-shaped anchor 20, whereby the bare wave of the stent can be accommodated by the sheath, thus avoiding the phenomenon that the bare wave of the stent is protruded after being hung on the stent fixing rod 22, where this phenomenon makes it difficult for the stent to be pushed into the sheath or which causes the sheath to be damaged when the stent is pushed into the sheath. In addition, the accommodating groove 23 accommodates the bare wave of the stent therein to fix the bare wave of the stent, so as to prevent the bare wave from shaking and damaging the sheath when the stent is retained inside the sheath. Preferably, since the stent fixing rod 22 is fixedly connected to the distal face 21*a* of the anchor body 21, after the stent is hooked on the stent fixing rod 22, the bare wave of the stent, which is the connecting arm of the stent, is inclined relative to the center thereof. In view of this, the depth of the accommodating groove 23 of this embodiment may be gradually increased from a proximal end to a distal end thereof, whereby the distal end of the accommodating groove 23 is inclined and approaches towards the center thereof, so as to better comply with the shape of a compressed bare wave coil of the stent, whereby the connecting arm of the stent may be completely placed in the accommodating groove 23, thus preventing the stent from being worn by the friction between the anchor body 21 and the connecting arm of the stent, and facilitating separation during the release process.

Preferably, as shown in FIG. 8, since a single wave of the stent is usually V-shaped, there are actually two connecting arms. Therefore, both sides of the stent fixing rod 22 are provided with the accommodating grooves 23, whereby the connecting arms connected to both sides of a hooking portion of the stent are accommodated in the accommodating grooves 23 on both sides of the stent fixing rod 22 respectively. Further, there are two stent fixing rods 22, and the two stent fixing rods 22 are opposite to each other in a radial direction of the distal face 21*a*. It will be understood that when there are two stent fixing rods 22, both sides of each stent fixing rod 22 are provided with the accommodating grooves 23. It should be noted that, in other embodiments, the number of the stent fixing rods 22 may be set according to actual needs, and the number of the accommodating grooves 23 at the sides of the stent fixing rods 22 and the provision manner may be improved according to needs, which are not limited thereto.

Figure 9:
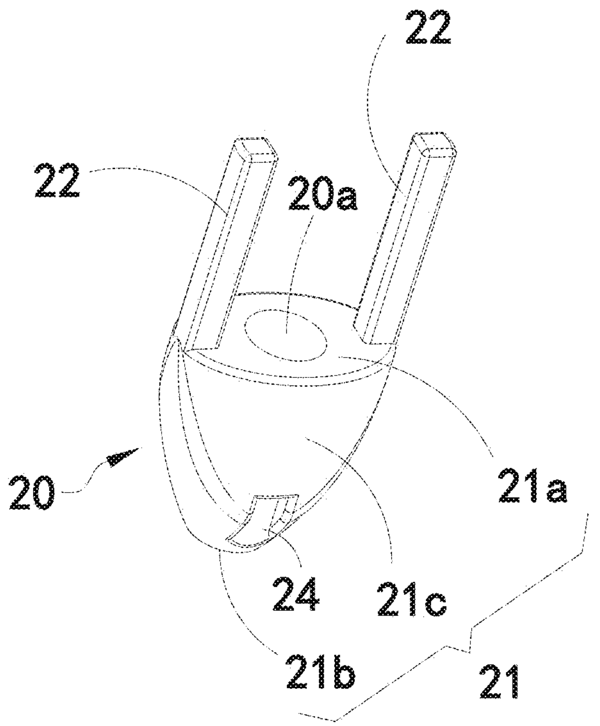
FIG. 9 is a schematic view depicting a structure of another U-shaped anchor in a sheath core assembly according to the present invention.

Referring to FIG. 9, as another implementation of the anchor body 21 of this embodiment, the anchor body 21 is axially provided with a via 20*a*. The anchor body 21 surrounds the sheath core 10 and is relatively fixed to the sheath core 10 through the via 20*a*. Both the distal face 21*a* and the proximal face 21*b* of the anchor body 21 are elliptic, whereby the anchor body 21 is approximately elliptically conical, which means that the proximal face 21*b* of the anchor body 21 is as close as possible to an outer periphery of the sheath core 10 to which the anchor body is relatively fixed, whereby the proximal end of the anchor body 21 has no step. The approximately elliptically conical anchor body 21 is provided such that there is a large gap between the outer periphery of the anchor body 21 and the sheath during the mounting process, and this gap allows passage of the connecting arm of the stent hooked on the stent fixing rod 22 without providing an additional accommodating groove 23. The structure is simplified, and the difficulty and cost of machining are greatly reduced. Preferably, an edge of a joint between the distal face 21*a* and the outer peripheral face 21*c* of the anchor body 21 is rounded to improve smoothness.

Further, as shown in FIG. 9, in order to reduce the volume of the U-shaped anchor 20 as much as possible and improve the smoothness of pushing besides realizing basic functions of the U-shaped anchor 20, when the anchor body 21 is arranged in an approximately elliptically conical shape, two stent fixing rods 22 are respectively fixed on edges of two long axes of the distal face of the anchor body 21, and after the via 20*a* is provided in the axial direction of the anchor body 21, larger connection positions are reserved on both sides of the long axes, whereby the U-shaped anchor 20 may be smaller and may be withdrawn more smoothly.

Figure 2:
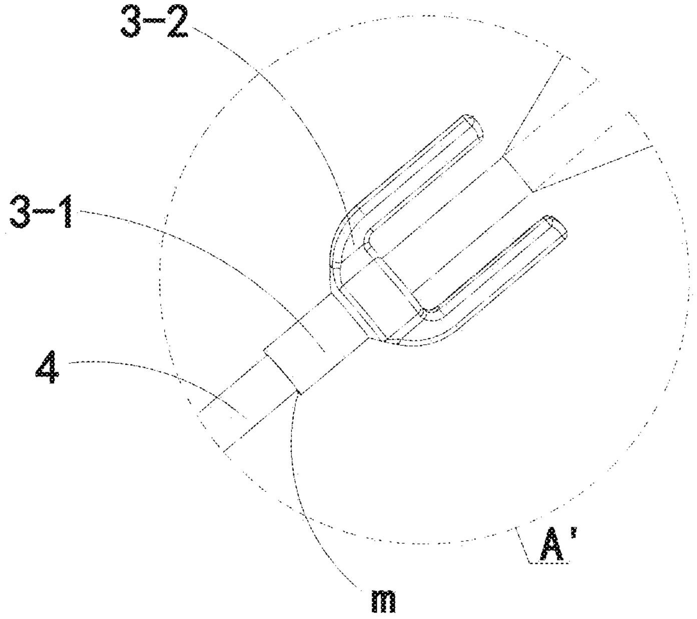
FIG. 2 is a schematic enlarged view of part A' in FIG. 1.
Figure 3:
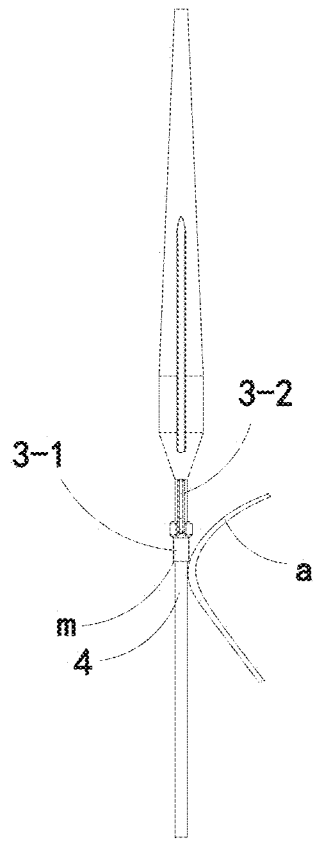
FIG. 3 is a schematic view of hooking a blood vessel wall by a step of a U-shaped anchor of an existing sheath core assembly.

As shown in FIG. 1 and FIG. 2, in the prior art, the U-shaped anchor 3 is a machined metal member, and the sheath core 4 is a stainless-steel metal member. In order to realize the relative fixation between the U-shaped anchor 3 and the sheath core 4, an additional welding zone 3-1 is required in the prior art to realize the welding fixation between the U-shaped anchor and the sheath core. To this end, referring to FIG. 8 and FIG. 9, in this embodiment, a welding groove 24 is recessed in the outer peripheral face 21*c* near the proximal end of the anchor body 21. After the anchor body 21 surrounds the sheath core 10 through the via 20*a*, the anchor body 21 and the sheath core 10 are welded and fixed by the welding groove 24. In this way, an additional welding zone is not required, thus avoiding the generation of a step and length increase caused by the welding zone. At the same time, the welding groove 24 of this embodiment is provided such that welding spots are built-in and not on the surface of the U-shaped anchor 20, thus avoiding damage to the blood vessels by uneven surfaces caused by welding.

Exemplarily, multiple welding grooves 24 are provided at intervals circumferentially along the arc-shaped outer peripheral face 21*c* of the anchor body 21. In this embodiment, multiple means two or more. In order to ensure the connection effect, the welding grooves 24 are provided at intervals circumferentially along the outer peripheral face 21*c* of the anchor body 21. Further, four welding grooves 24 are provided at equal intervals circumferentially.

As shown in FIG. 7 and FIG. 8, in other embodiments, the anchor body 21 is further axially provided with two symmetrical pulling wire holes 25. The pulling wire holes 25 are configured for passage of pulling wires pulling the stent into the sheath. Further, the pulling wire holes 25 are opposite to exhaust grooves 41 on the tip 40 in the sheath core assembly 100. The pulling wire holes 25 and the exhaust grooves 41 of the tip 40 are located on the same side, whereby the pulling wires pass through the tip 40 in a straight manner.

In the sheath core assembly 100 of this embodiment, an outer periphery of an anchor body is arranged as an arc-shaped transition face, and a welding groove is recessed in the arc-shaped transition face, whereby a distal end of the anchor body has no step, thus solving the problem of difficulty in pushing and withdrawing due to the existence of steps in a welding zone, and greatly improving the smoothness of withdrawal of a delivery device from blood vessels, and especially curved blood vessels. In addition, built-in welding spots avoid damage to the blood vessels by uneven surfaces caused by welding, thus further improving the smoothness.

Figure 4:
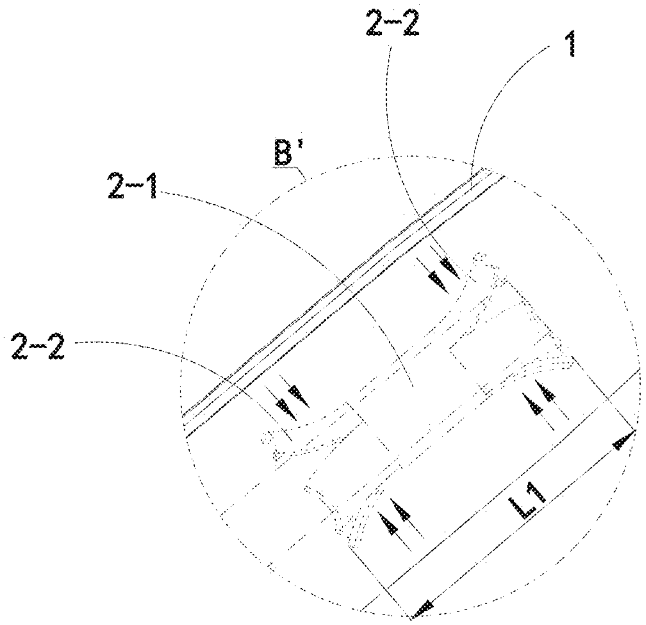
FIG. 4 is a schematic enlarged view of part B' in FIG. 1.
Figure 5:
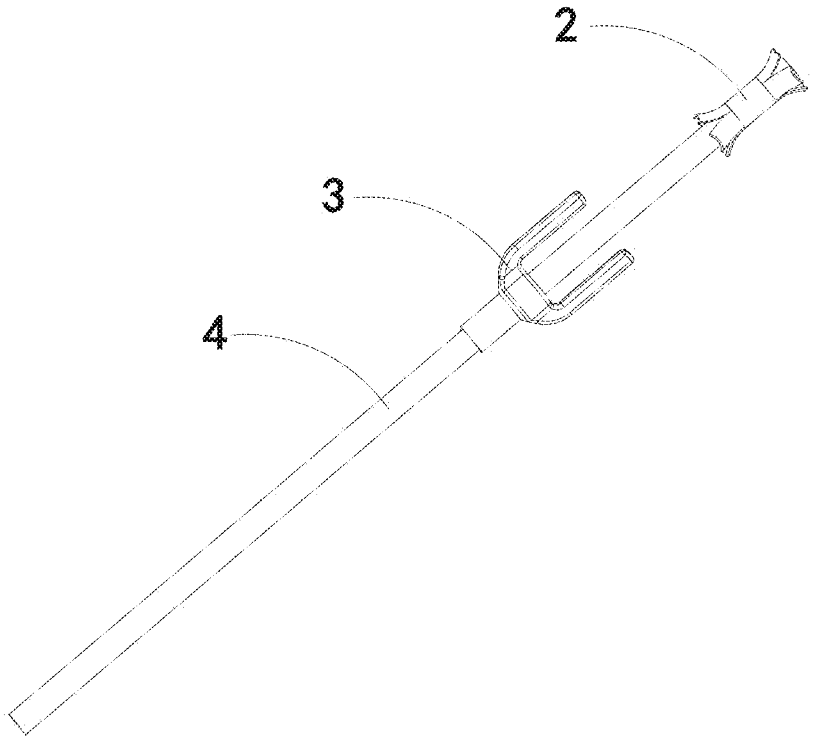
FIG. 5 is a schematic view of an existing sheath core assembly with a tip hidden.

Further, referring to FIG. 1 and FIG. 4, as mentioned in the Background Art, the sheath core assembly of the existing delivery device further includes a bifurcation tube 2 for connecting and fixing the tip 1 to the stainless-steel tube 4. The structure of the existing bifurcation tube 2 is shown in FIG. 4. The bifurcation tube 2 has a welding zone 2-1 and a fixing zone 2-2. The two functional zones are arranged at different positions of the bifurcation tube 2, resulting in a large overall length L1 of the bifurcation tube. Also, since the bifurcation tube 2 is buried in the tip 1, the length L2 of a high-hardness zone of the tip 1 is large, thus reducing the compliance of the tip 1 and affecting the pushing and withdrawing of the punctured tissue of the sheath core 4 in the blood vessel. In addition, when the bifurcation tube 2 is used for injection molding of the tip 1, the fixing zone 2-2 of the bifurcation tube 2 will be deformed or even broken in an arrow direction due to the injection molding pressure (the pressure direction is as indicated by arrows in FIG. 4), which will reduce the connection strength and seriously lead to connection failure.

In view of this, as an optimized scheme, on the basis of solving the problem of shifting of the stent or difficulty in withdrawing the stent hooked on the vascular wall caused by the step, this embodiment further solves the problem of fracture failure.

In an optimized scheme, the sheath core assembly of this embodiment further includes a connector 30 surrounding a distal end of the sheath core 10 and configured to connect the sheath core 10 to the tip 40 on the basis of the foregoing. In a further optimized embodiment, the sheath core assembly includes a sheath core 10, a U-shaped anchor 20 surrounding the sheath core 10 and relatively fixed to the sheath core 10, and a connector 30 surrounding a distal end of the sheath core 10 and configured to connect the sheath core 10 to the tip 40.

Exemplarily, a groove is recessed in an outer peripheral surface of the connector 30, and the connector is relatively fixed to the sheath core and the tip through the groove. With the groove, the thickness of the groove can be reduced, thus realizing the welding between the connector 30 and the sheath core 10 through the groove. In addition, during the injection molding process of the tip 40, glue injection liquid of the tip 40 may enter the groove to realize the connection between the tip 40 and the connector 30, while forming axial and circumferential limits.

Preferably, the connector 30 for connecting the sheath core 10 to the tip 40 is a solid metal member. Exemplarily, the connector is machined from a stainless-steel material. The connector 30 is axially provided with an axial hole 31. The connector 30 surrounds the distal end of the sheath core 10 and is relatively fixed to the sheath core 10 through the axial hole 31. A groove is recessed in an outer peripheral surface of the connector 30, and the connector 30 is relatively fixed to the sheath core 10 and the tip 40 through the groove.

Exemplarily, the connector 30 has a polygonal radial cross-section, whereby an outer peripheral face of the connector 30 includes multiple surfaces, and the groove is recessed in the outer peripheral surface of the connector 30. This arrangement further enhances the connection and improves the axial and circumferential limits. The groove may be provided on one surface, grooves are provided on multiple surfaces, or multiple grooves are provided on one surface, which may be specifically set according to the situation. It should also be noted that the radial cross-section of the connector 30 may be of other shapes, and is not limited to a polygon. For example, the radial cross-section of the connector may be round, and the connector 30 may be a cylindrical body with a groove recessed in a surface of the cylindrical body.

Figure 11:
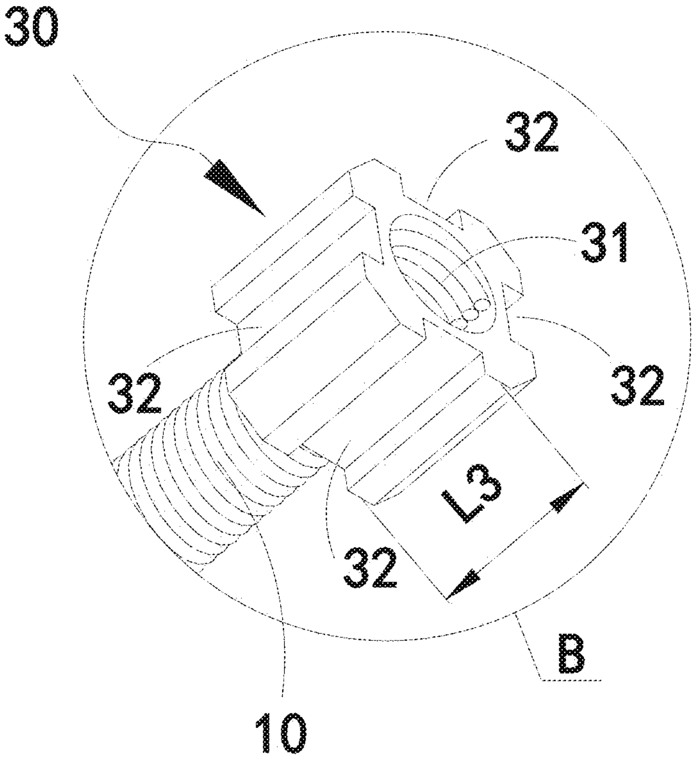
FIG. 11 is a schematic enlarged view of part B in FIG. 10.

As shown in FIG. 11, as one embodiment, the connector 30 has a quadrilateral radial cross-section, whereby the outer peripheral face of the connector 30 includes four surfaces. Preferably, for ease of machining, the connector 30 is a cuboid or a cube, where a circumferential surface of the cuboid or the cube is provided with a groove. Exemplarily, each outer peripheral surface of the cuboid or the cube is provided with a first groove 32 cut from a distal face and a proximal face of the connector 30, so as to form a strip-shaped groove on each outer peripheral surface. The groove bottom of the strip-shaped groove is welded to the sheath core 10 to achieve relative fixation between the connector 30 and the sheath core 10.

Figure 12:
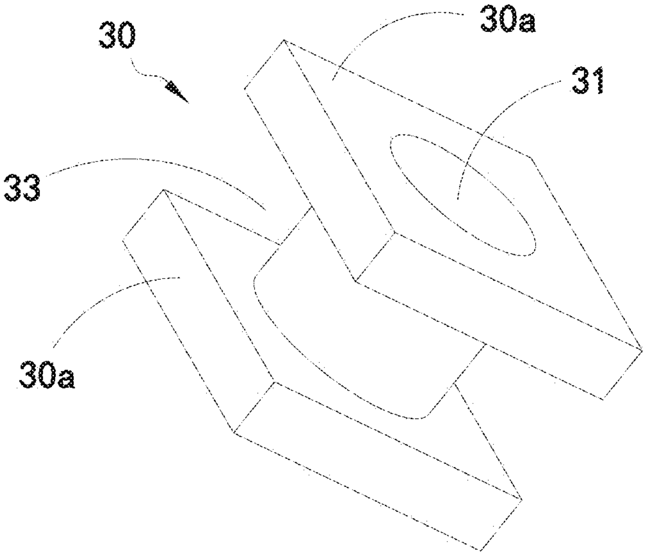
FIG. 12 is a schematic view depicting a structure of another connector in a sheath core assembly according to the present invention.

As shown in FIG. 12, as another embodiment, the connector 30 has a quadrilateral radial cross-section, whereby the outer peripheral face of the connector 30 includes four surfaces. Preferably, for ease of machining, the connector 30 is a cuboid or a cube, where a circumferential surface of the cuboid or the cube is provided with a second groove 33 not cut from the distal face and the proximal face of the connector 30. Exemplarily, the second groove 33 is an annular groove surrounding an outer peripheral surface of the cuboid or the cube. The groove bottom of the annular groove is welded to the sheath core 10 to achieve relative fixation between the connector 30 and the sheath core 10.

Figure 13:
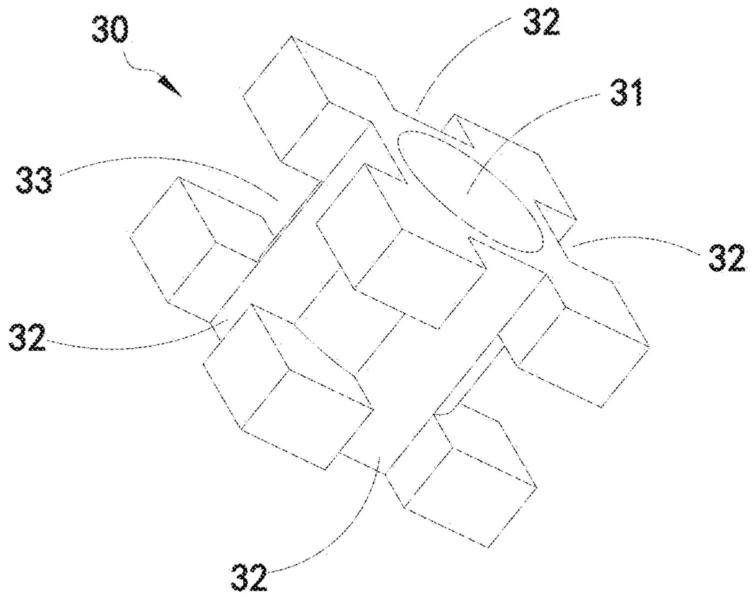
FIG. 13 is a schematic view depicting a structure of yet another connector in a sheath core assembly according to the present invention.

As shown in FIG. 13, as yet another embodiment, the connector 30 has a quadrilateral radial cross-section, whereby the outer peripheral face of the connector 30 includes four surfaces. Preferably, for ease of machining, the connector 30 is a cuboid or a cube, where a circumferential surface of the cuboid or the cube is provided with a groove. Exemplarily, each outer peripheral surface of the cuboid or the cube is provided with a first groove 32 cut from a distal face and a proximal face of the connector 30, so as to form a strip-shaped groove on each outer peripheral surface. At the same time, a circumferential surface of the cuboid or the cube is provided with a second groove 33 not cut from the distal face and the proximal face of the connector 30. The second groove 33 is provided annularly. The annular groove extends through the strip-shaped groove. The groove bottoms of the grooves are welded to the sheath core 10 to achieve relative fixation between the connector 30 and the sheath core 10.

Figure 14:
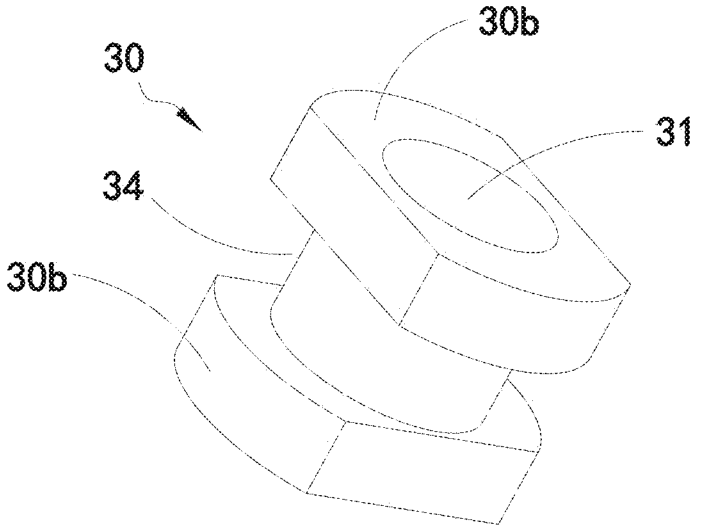
FIG. 14 is a schematic view depicting a structure of yet another connector in a sheath core assembly according to the present invention.

As shown in FIG. 14, as an implementation that the connector 30 has a quadrilateral radial cross-section, a third groove 34 is recessed circumferentially along the outer peripheral face of the connector 30. The third groove 34 does not extend into the distal face and the proximal face of the connector 30, whereby blocking portions **30*b* are formed at a proximal side and a distal side of the third groove 34 respectively. The blocking portions 30*b* have quadrilateral radial cross-sections, and two opposite sides of the quadrilateral are straight lines while the other two opposite sides are arc lines, whereby two opposite faces of the blocking portion 30*b* are arc faces, and the arc faces of the two blocking portions 30*b* at the proximal side and the distal side are interlaced in azimuth. The interlaced blocking portions 30*b*** further improve the strength of the circumferential limit and the axial limit.

In this embodiment, the welding zone and the circumferential fixing zone of the connector 30 are designed in the same groove. As shown in FIG. 11 compared to FIG. 4, an overall length L3 of the connector 30 of this embodiment is obviously smaller than a length L4 of the existing bifurcation tube, and the overall length is reduced. As shown in FIG. 7, after being buried in the tip 40, the length L4 of a high-hardness zone of the tip 40 is smaller, and the compliance is better. At the same time, the overall structure of the connector 30 is more stable, and the connector will not be deformed during injection molding of the tip 40 and is more reliably connected to the tip 40. The sheath core assembly 100 of this embodiment not only solves the problem of difficulty in withdrawing caused by the steps in the welding zone, but also solves the problems of difficulty in pushing and withdrawing, and fracture failure caused by the existing bifurcation tube.

Figure 6:
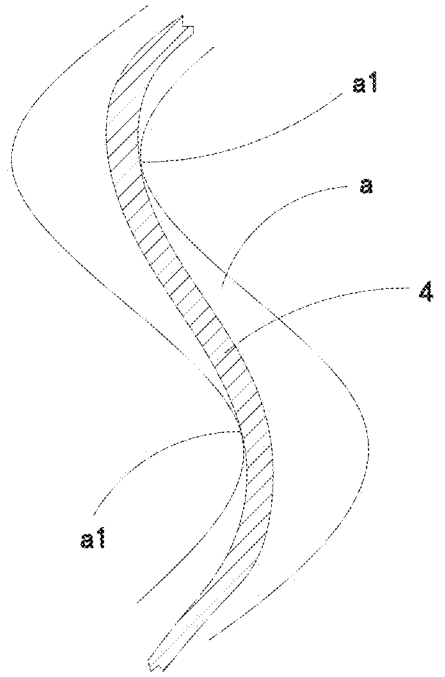
FIG. 6 is a schematic view of a sheath core of an existing sheath core assembly in a blood vessel.

Further, as shown in FIG. 1 and FIG. 6, as mentioned in the Background Art, the existing sheath core assembly includes a sheath core 4. The sheath core 4 is usually a stainless-steel tube, which leads to high hardness and poor compliance of the distal end of the sheath core 4. The sheath core cannot bend or recover in time in compliance with the shape of a blood vessel a, and the blood vessel a obstructs the sheath core 4 to form a resistance zone a1, which will make it difficult to push or withdraw the sheath core.

In view of this, as an optimized scheme, on the basis of solving the problem of shifting of the stent or difficulty in withdrawing the stent hooked on the vascular wall caused by the step, this embodiment further solves the problem of the difficulty in pushing and withdrawing caused by high hardness of the distal end of the sheath core.

In an optimized scheme, the sheath core assembly of this embodiment includes a sheath core 10 and a U-shaped anchor 20 surrounding the sheath core 10 and relatively fixed to the sheath core 10. In a more optimized scheme, the sheath core assembly 100 may further include a tip 40 wrapping the distal end of the sheath core 10. It should be noted that the tip 40 does not constitute a necessary feature of this embodiment to solve the problems presented therein. It should be noted that in addition to the structure of the sheath core 10 and the U-shaped anchor 20 in this embodiment, the structure of other features may refer to the prior art or other embodiments of this application, and the structure of other features is not limited.

Figure 10:
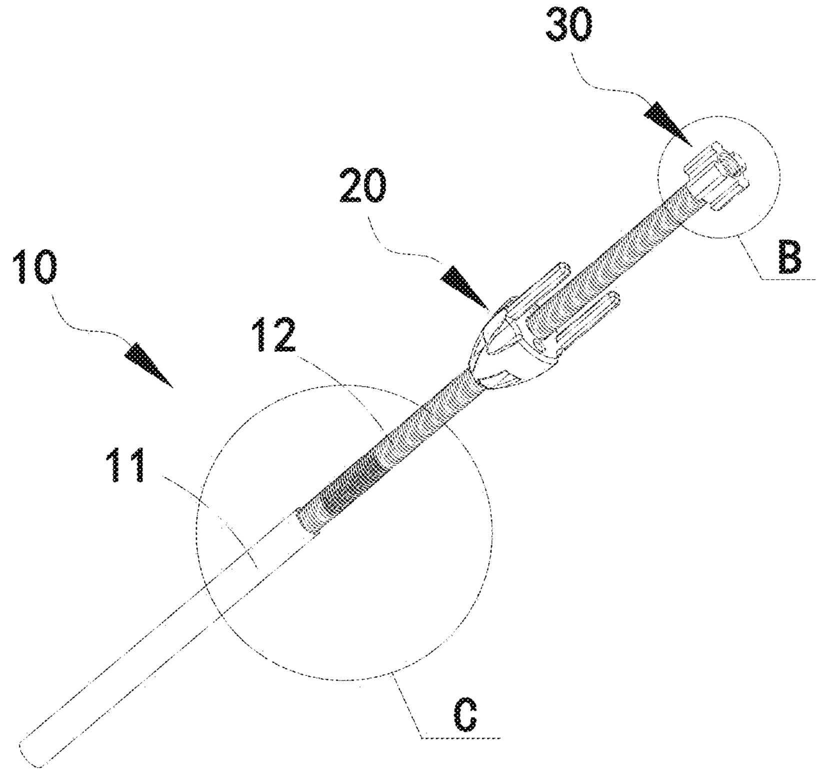
FIG. 10 is a schematic view of a sheath core assembly with a tip hidden according to the present invention.
Figure 15:
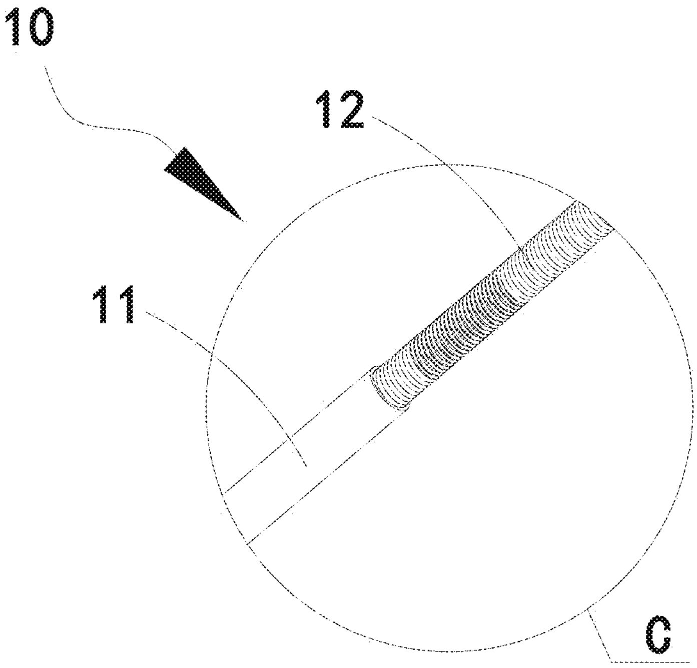
FIG. 15 is a schematic enlarged view of part C in FIG. 10.

Specifically, as shown in FIG. 7, FIG. 10, and FIG. 15, the sheath core 10 of this embodiment includes a first tube body 11 and a second tube body 12 retained inside the first tube body 11. A distal end of the second tube body 12 extends out of a distal face of the first tube body 11, and the compliance of the second tube body 12 is superior to that of the first tube body 11. The U-shaped anchor 20 surrounds the second tube body 12 and is relatively fixed to the second tube body 12. In this embodiment, the second tube body 12 having better compliance is retained inside the first tube body 11 and extends out of the distal end of the first tube body 11, thereby improving the hardness of the distal end of the sheath core 10, improving the compliance of the distal end of the sheath core 10, and solving the problem of difficulty in pushing and withdrawing caused by high hardness of the distal end of the sheath core 10.

Exemplarily, referring to FIG. 15, the first tube body 11 is a cylindrical tube, preferably a stainless-steel tube. The second tube body 12 is a helical tube, having a helical structure similar to a spring. The stainless-steel tube wraps an outer wall of the helical tube, and a distal end of the helical tube extends out of a distal end of the stainless-steel tube. The compliance of the helical tube is superior to that of the stainless-steel tube, and the rigidity of the distal end is ensured while the flexibility of the proximal end of the sheath core 10 is ensured, and the main body of the sheath core 10 has sufficient pushing property.

Figure 16:
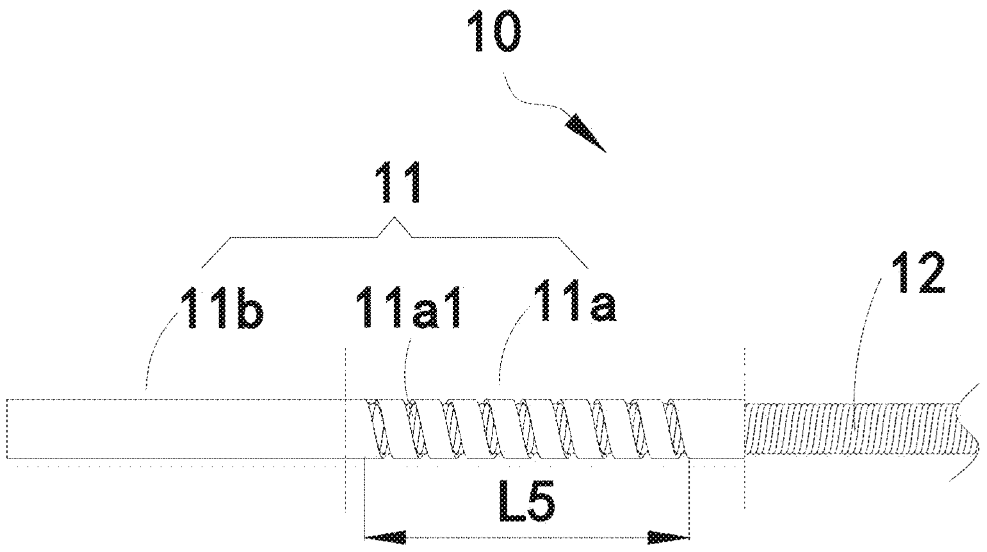
FIG. 16 is a schematic view 1 depicting a partial structure of a sheath core in a sheath core assembly according to the present invention.
Figure 17:
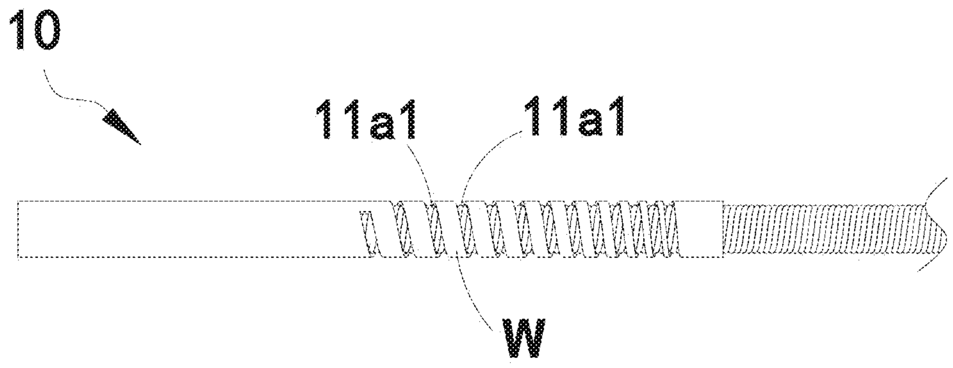
FIG. 17 is a schematic view 2 depicting a partial structure of a sheath core in a sheath core assembly according to the present invention.

There is a gap between the helical tube and the stainless-steel tube because of the sleeve connection between the helical tube and the stainless steel tube, and there is usually a final cleaning process in the manufacturing process, in which cleaning liquid will enter the gap and flush the gap at the same time. In view of this, as shown in FIG. 16 and FIG. 17, the first tube body 11 of this embodiment includes a first section 11*a* that surrounds the outside of the second tube body 12 and a second section 11*b* connected to the distal end of the first section 11*a*. The first section 11*a* is provided with a notch 11*a*1. The sleeved stainless-steel tube and helical tube can be fully flushed through the notch 11*a*1, and flushing liquid can easily flow out of the notch after the cleaning process, thus avoiding the cleaning liquid remaining in the gap. At the same time, the hardness of a sleeving section between the first tube body 11 and the second tube body 12 is transitioned to avoid high local hardness, whereby the compliance of the sheath core 10 is better. It should be noted that the distal end of the first section 11*a* is closed so that the end has a closed section by which the distal ends of the first tube body 11 and the second tube body 12 can be welded.

Preferably, multiple notches 11*a*1 are provided at intervals along an axial direction of the first section 11*a*, and the entire sleeving section can be fully cleaned by the multiple notches 11*a*1 in the axial direction while the hardness of the entire section is transitioned. In one embodiment, the adjacent notches 11*a*1 on the first section 11*a* are provided at equal intervals from a proximal end of the first section 11*a* to the distal end thereof. In another embodiment, the adjacent notches 11*a*1 on the first section 11*a* are provided at gradually reducing intervals from a proximal end of the first section 11*a* to the distal end thereof. The distance between the proximal and distal notches 11*a*1 is gradually reduced, whereby the adjacent notches 11*a*1 are gradually increased from the proximal end to the distal end, and the hardness transition from the proximal end to the distal end is better, and the flexibility towards the distal end is better.

With continued reference to FIG. 16 and FIG. 17, in other embodiments, the notch 11*a*1 is a helical notch which extends helically along an axial direction of the first section 11*a* in order to facilitate the cleaning of the gap within the entire sleeving section at the same time as machining. Preferably, as an implementation, the adjacent notches 11*a*1 on the first section 11*a* are provided at equal intervals W from a proximal end of the first section 11*a* to the distal end thereof. As another embodiment, the adjacent notches 11*a*1 on the first section 11*a* are provided at gradually reducing intervals W from a proximal end of the first section 11*a* to the distal end thereof, whereby the adjacent notches 11*a*1 are gradually increased from the proximal end to the distal end, and the transition from the proximal end to the distal end is better, and the flexibility towards the distal end is better.

In the sleeving process, preferably, as shown in FIG. 16, a length L5 between the distal and the proximal notches 11*a*1 on the first section 11*a* of this embodiment is 5-200 mm. This length orientation ensures as much as possible the compliance of the transition section and the rigidity of other sections of the sheath core 10, whereby the main body of the sheath core 10 has sufficient pushing property.

In this embodiment, the sheath core 10 is designed by combining a helical tube and a stainless-steel tube. The stainless-steel tube wraps an outer wall of the helical tube. The sheath core adopts the structure that the helical tube is located at a distal end while the stainless-steel tube is located at a proximal end. A notch is provided at a distal end of the stainless-steel tube, and the distal end is a closed section for being welded and fixed to the helical tube and sealing the notch. The notch achieves a flexible even transition between the helical tube and the stainless-steel tube, ensures the flexibility of the distal end of the sheath core 10 and the rigidity of the proximal end, and ensures that a main body of the sheath core 10 has sufficient pushing property. The sheath core assembly 100 of this embodiment not only solves the problem of difficulty in withdrawing caused by the steps in the welding zone, but also solves the problem of difficulty in pushing and withdrawing caused by the poor compliance of the distal end of the existing sheath core 10.

Embodiment 2

Referring to FIG. 1 and FIG. 4, as mentioned in the Background Art, the sheath core assembly of the existing delivery device further includes a bifurcation tube 2 for connecting and fixing the tip 1 to the stainless-steel tube 4. The structure of the existing bifurcation tube 2 is shown in FIG. 4. The bifurcation tube 2 has a welding zone 2-1 and a fixing zone 2-2. The two functional zones are arranged at different positions of the bifurcation tube 2, resulting in a large overall length L1 of the bifurcation tube. Also, since the bifurcation tube 2 is buried in the tip 1, the length L2 of a high-hardness zone of the tip 1 is large, thus reducing the compliance of the tip 1 and affecting the pushing and withdrawing of the punctured tissue of the sheath core 4 in the blood vessel. In addition, when the bifurcation tube 2 is used for injection molding of the tip 1, the fixing zone 2-2 of the bifurcation tube 2 will be deformed or even broken in an arrow direction due to the injection molding pressure (the pressure direction is as indicated by arrows in FIG. 4), which will reduce the connection strength and seriously lead to the connection failure.

In view of this, this embodiment provides a sheath core assembly, so as to solve the problem of fracture failure.

Referring to FIG. 7 and FIG. 10, this embodiment provides a sheath core assembly 100. The sheath core assembly 100 of this embodiment includes a sheath core 10, a U-shaped anchor surrounding the sheath core 10 and relatively fixed to the sheath core 10, and a connector 30 surrounding the distal end of the sheath core 10 and configured to connect the sheath core 10 to a tip 40. Preferably, the sheath core assembly 100 may further include a tip 40 wrapping the distal end of the sheath core 10. It should be noted that the tip 40 does not constitute a necessary feature of this embodiment to solve the problems presented therein. The structure of the sheath core 10 in this embodiment may refer to the prior art. For example, the sheath core may be a stainless-steel tube. Preferably, a novel sheath core structure may also be provided. A detailed implementation of the novel sheath core structure may refer to the following Embodiment 3. The specific structure of the U-shaped anchor is described in detail with reference to the U-shaped anchor 20 in Embodiment 1 and will not be described herein. In this embodiment, the structure of the connector 30 surrounding the distal end of the sheath core 10 and configured to connect the sheath core 10 to the tip 40 is mainly described in detail. It should be noted that in addition to the structure of the connector 30 in this embodiment, the structure of other features may refer to the prior art or other embodiments of this application, and the structure of other features is not limited.

As shown in FIG. 7, FIG. 10, and FIG. 11, the connector 30 for connecting the sheath core 10 to the tip 40 in this embodiment is a solid metal member. Exemplarily, the connector is machined from a stainless-steel material. The connector 30 is axially provided with an axial hole 31. The connector 30 surrounds the distal end of the sheath core 10 and is relatively fixed to the sheath core 10 through the axial hole 31. A groove is recessed in an outer peripheral surface of the connector 30, and the connector 30 is relatively fixed to the sheath core 10 and the tip 40 through the groove. With the groove, the thickness of the groove can be reduced, thus realizing the welding between the connector 30 and the sheath core 10 through the groove. In addition, during the injection molding process of the tip 40, glue injection liquid of the tip 40 may enter the groove to realize the connection between the tip 40 and the connector 30, while forming axial and circumferential limits.

Exemplarily, the connector 30 has a polygonal radial cross-section, whereby an outer peripheral face of the connector 30 includes multiple surfaces, and the groove is recessed in the outer peripheral surface of the connector 30. This arrangement further enhances the connection and improves the axial and circumferential limits. The groove may be provided on one surface, grooves are provided on multiple surfaces, or multiple grooves are provided on one surface, which may be specifically set according to the situation. It should also be noted that the radial cross-section of the connector 30 may be of other shapes, and is not limited to a polygon. For example, the radial cross-section of the connector may be round, and the connector 30 may be a cylindrical body with a groove recessed in a surface of the cylindrical body.

As shown in FIG. 11, as an embodiment, the connector 30 has a quadrilateral radial cross-section, whereby the outer peripheral face of the connector 30 includes four surfaces. Preferably, for ease of machining, the connector 30 is a cuboid or a cube, where a circumferential surface of the cuboid or the cube is provided with a groove. Exemplarily, each outer peripheral surface of the cuboid or the cube is provided with a first groove 32 cut from a distal face and a proximal face of the connector 30, so as to form a strip-shaped groove on each outer peripheral surface. The groove bottom of the strip-shaped groove is welded to the sheath core 10 to achieve relative fixation between the connector 30 and the sheath core 10.

As shown in FIG. 12, as another embodiment, the connector 30 has a quadrilateral radial cross-section, whereby the outer peripheral face of the connector 30 includes four surfaces. Preferably, for ease of machining, the connector 30 is a cuboid or a cube, where a circumferential surface of the cuboid or the cube is provided with a second groove 33 that is not cut from the distal face and the proximal face of the connector 30. Exemplarily, the second groove 33 is an annular groove surrounding an outer peripheral surface of the cuboid or the cube. The groove bottom of the annular groove is welded to the sheath core 10 to achieve relative fixation between the connector 30 and the sheath core 10.

As shown in FIG. 13, as yet another embodiment, the connector 30 has a quadrilateral radial cross-section, whereby the outer peripheral face of the connector 30 includes four surfaces. Preferably, for ease of machining, the connector 30 is a cuboid or a cube, where a circumferential surface of the cuboid or the cube is provided with a groove. Exemplarily, each outer peripheral surface of the cuboid or the cube is provided with a first groove 32 cut from a distal face and a proximal face of the connector 30, so as to form a strip-shaped groove on each outer peripheral surface. At the same time, a circumferential surface of the cuboid or the cube is provided with a second groove 33 not cut from the distal face and the proximal face of the connector 30. The second groove 33 is provided annularly. The annular groove extends through the strip-shaped groove. The groove bottoms of the grooves are welded to the sheath core 10 to achieve relative fixation between the connector 30 and the sheath core 10.

As shown in FIG. 14, as an embodiment that the connector 30 has a quadrilateral radial cross-section, a third groove 34 is recessed circumferentially along the outer peripheral face of the connector 30. The third groove 34 is not cut from the distal face and the proximal face of the connector 30, whereby blocking portions 30*b* are formed at a proximal side and a distal side of the third groove 34 respectively. The blocking portions 30*b* have quadrilateral radial cross-sections, and two opposite sides of the quadrilateral are straight lines while the other two opposite sides are arc lines, whereby two opposite faces of the blocking portion 30*b* are arc faces, and the arc faces of the two blocking portions 30*b* at the proximal side and the distal side are interlaced in azimuth. The interlaced blocking portions 30*b* further improve the strength of the circumferential limit and the axial limit.

In this embodiment, the welding zone and the circumferential fixing zone of the connector 30 are designed in the same groove. As shown in FIG. 11, compared to FIG. 4, the overall length L3 of the connector 30 of this embodiment is obviously smaller than the length L4 of the existing bifurcation tube, and the overall length is reduced. As shown in FIG. 7, after being buried in the tip 40, the length L4 of a high-hardness zone of the tip 40 is smaller, and the compliance is better. At the same time, the overall structure of the connector 30 is more stable, and the connector will not be deformed during injection molding of the tip 40 and is more reliably connected to the tip 40. The sheath core assembly 100 of this embodiment solves the problems of difficulty in pushing and withdrawing and fracture failure caused by the existing bifurcation tube. Definitely, when the U-shaped anchor of this embodiment adopts the U-shaped anchor 20 of Embodiment 1, this embodiment solves the problems of difficulty in pushing and withdrawing and fracture failure while further solving the problem of difficulty in withdrawing caused by the steps in the welding zone.

Further, as shown in FIG. 1 and FIG. 6, as mentioned in the Background Art, the existing sheath core assembly includes a sheath core 4. The sheath core 4 is usually a stainless-steel tube, which leads to high hardness and poor compliance of a distal end of the sheath core 4. The sheath core cannot bend or recover in time in compliance with the shape of a blood vessel a, and the blood vessel a obstructs the sheath core 4 to form a resistance zone a1, which will make it difficult to push or withdraw the sheath core.

In view of this, as an optimized scheme, on the basis of solving the problem of fracture failure, this embodiment further solves the problem of difficulty in pushing and withdrawing caused by high hardness of the distal end of the sheath core.

In an optimized scheme, the sheath core assembly of this embodiment includes a sheath core 10 and a U-shaped anchor 20 surrounding the sheath core 10 and relatively fixed to the sheath core 10. Preferably, the sheath core assembly 100 may further include a tip 40 wrapping the distal end of the sheath core 10. It should be noted that the tip 40 does not constitute a necessary feature of this embodiment to solve the problems presented therein. It should be noted that in addition to the structure of the sheath core 10 and the U-shaped anchor 20 in this embodiment, the structure of other features may refer to the prior art or other embodiments of this application, and the structure of other features is not limited.

Specifically, as shown in FIG. 7, FIG. 10, and FIG. 15, the sheath core 10 of this embodiment includes a first tube body 11 and a second tube body 12 retained in the first tube body 11. A distal end of the second tube body 12 extends out of the distal face of the first tube body 11, and the compliance of the second tube body 12 is superior to that of the first tube body 11. The U-shaped anchor 20 surrounds the second tube body 12 and is relatively fixed to the second tube body 12. In this embodiment, the second tube body 12 having better compliance surrounds the first tube body 11 and extends out of the distal end of the first tube body 11, thereby improving the hardness of the distal end of the sheath core 10, improving the compliance of the distal end of the sheath core 10, and solving the problem of difficulty in pushing and withdrawing caused by high hardness of the distal end of the sheath core 10.

Exemplarily, referring to FIG. 15, the first tube body 11 is a cylindrical tube, preferably a stainless-steel tube. The second tube body 12 is a helical tube, having a helical structure similar to a spring. The stainless-steel tube wraps an outer wall of the helical tube, and a distal end of the helical tube extends out of the distal end of the stainless-steel tube. The compliance of the helical tube is superior to that of the stainless-steel tube, and the rigidity of the distal end is ensured while the flexibility of the proximal end of the sheath core 10 is ensured, and a main body of the sheath core 10 has sufficient pushing property.

There is a gap between the helical tube and the stainless-steel tube because of the sleeve connection between the helical tube and the stainless steel tube, and there is usually a final cleaning process in the manufacturing process, in which cleaning liquid will enter the gap and flush the gap at the same time. In view of this, as shown in FIG. 16 and FIG. 17, the first tube body 11 of this embodiment includes a first section 11*a* surrounding the second tube body 12 and a second section 11*b* connected to a distal end of the first section 11*a*. The first section 11*a* is provided with a notch 11*a*1. The sleeved stainless-steel tube and helical tube can be fully flushed through the notch 11*a*1, and flushing liquid can easily flow out of the notch after the cleaning process, thus avoiding the cleaning liquid remaining in the gap. At the same time, the hardness of a sleeving section between the first tube body 11 and the second tube body 12 is transitioned to avoid high local hardness, whereby the compliance of the sheath core 10 is better. It should be noted that the distal end of the first section 11*a* is closed so that the end has a closed section by which the distal ends of the first tube body 11 and the second tube body 12 can be welded.

Preferably, multiple notches 11*a*1 are provided at intervals along an axial direction of the first section 11*a*, and the entire sleeving section can be fully cleaned by the multiple notches 11*a*1 in the axial direction while the hardness of the entire section is transitioned. As an embodiment, the adjacent notches 11*a*1 on the first section 11*a* are provided at equal intervals from a proximal end of the first section 11*a* to the distal end thereof. As another embodiment, the adjacent notches 11*a*1 on the first section 11*a* are provided at gradually reducing intervals from a proximal end of the first section 11*a* to the distal end thereof. The distance between the proximal and distal notches 11*a*1 is gradually reduced, whereby the adjacent notches 11*a*1 are gradually increased from the proximal end to the distal end, and the hardness transition from the proximal end to the distal end is better, and the flexibility towards the distal end is better.

With continued reference to FIG. 16 and FIG. 17, in other embodiments, the notch 11*a*1 is a helical notch which extends helically along an axial direction of the first section 11*a* in order to facilitate the cleaning of the gap within the entire sleeving section at the same time as machining. Preferably, as an embodiment, the adjacent notches 11*a*1 on the first section 11*a* are provided at equal intervals W from a proximal end of the first section 11*a* to the distal end thereof. As another embodiment, the adjacent notches 11*a*1 on the first section 11*a* are provided at gradually reducing intervals W from a proximal end of the first section 11*a* to the distal end thereof, whereby the adjacent notches 11*a*1 are gradually increased from the proximal end to the distal end, and the transition from the proximal end to the distal end is better, and the flexibility towards the distal end is better.

In the sleeving process, preferably, as shown in FIG. 16, the length L5 between the distal and the proximal notches 11*a*1 on the first section 11*a* of this embodiment is 5-200 mm. This length orientation ensures as much as possible the compliance of the transition section and the rigidity of other sections of the sheath core 10, whereby the main body of the sheath core 10 has sufficient pushing property.

In this embodiment, the sheath core 10 is designed by combining a helical tube and a stainless-steel tube. The stainless-steel tube wraps an outer wall of the helical tube. The sheath core adopts the structure that the helical tube is located at a distal end while the stainless-steel tube is located at a proximal end. A notch is provided at a distal end of the stainless-steel tube, and the distal end is a closed section for being welded and fixed to the helical tube and sealing the notch. The notch achieves a flexible even transition between the helical tube and the stainless-steel tube, ensures the flexibility of the distal end of the sheath core 10 and the rigidity of the proximal end, and ensures that a main body of the sheath core 10 has sufficient pushing property. The sheath core assembly 100 of this embodiment not only solves the problem of fracture failure, but also solves the problem of difficulty in pushing and withdrawing caused by the poor compliance of the distal end of the existing sheath core 10.

Embodiment 3

As shown in FIG. 1 and FIG. 6, as mentioned in the Background Art, the existing sheath core assembly includes a sheath core 4. The sheath core 4 is usually a stainless-steel tube, which leads to high hardness and poor compliance of a distal end of the sheath core 4. The sheath core cannot bend or recover in time in compliance with the shape of a blood vessel a, and the blood vessel a obstructs the sheath core 4 to form a resistance zone a1, which will make it difficult to push or withdraw the sheath core.

In view of this, this embodiment provides a novel sheath core assembly, so as to solve the problem of difficulty in pushing and withdrawing caused by high hardness of the distal end of the sheath core.

Referring to FIG. 7 and FIG. 10, the sheath core assembly 100 of this embodiment includes a sheath core 10 and a U-shaped anchor surrounding the sheath core 10 and relatively fixed to the sheath core 10. In addition, the sheath core assembly 100 may further include a tip 40 wrapping a distal end of the sheath core 10. The specific structure of the U-shaped anchor in this embodiment refers to the U-shaped anchor 20 in Embodiment 1 and will not be described herein. This embodiment mainly describes in detail the structure of the sheath core in the sheath core assembly 100. It should be noted that in addition to the structure of the sheath core 10 in this embodiment, the structure of other features may refer to the prior art or other embodiments of this application, and the structure of other features is not limited.

Specifically, as shown in FIG. 7, FIG. 10, and FIG. 15, the sheath core 10 of this embodiment includes a first tube body 11 and a second tube body 12 retained in the first tube body 11. The distal end of the second tube body 12 extends out of a distal face of the first tube body 11, and the compliance of the second tube body 12 is superior to that of the first tube body 11. The U-shaped anchor 20 surrounds the second tube body 12 and is relatively fixed to the second tube body 12. In this embodiment, the second tube body 12 having better compliance surrounds the first tube body 11 and extends out of the distal end of the first tube body 11, thereby improving the hardness of the distal end of the sheath core 10, improving the compliance of the distal end of the sheath core 10, and solving the problem of difficulty in pushing and withdrawing caused by high hardness of the distal end of the sheath core 10.

Exemplarily, referring to FIG. 15, the first tube body 11 is a cylindrical tube, preferably a stainless-steel tube. The second tube body 12 is a helical tube, having a helical structure similar to a spring. The stainless-steel tube wraps an outer wall of the helical tube, and the distal end of the helical tube extends out of a distal end of the stainless-steel tube. The compliance of the helical tube is superior to that of the stainless-steel tube, and the rigidity of the distal end is ensured while the flexibility of the proximal end of the sheath core 10 is ensured, and a main body of the sheath core 10 has sufficient pushing property.

There is a gap between the helical tube and the stainless-steel tube because of the sleeve connection between the helical tube and the stainless-steel tube, and there is usually a final cleaning process in the manufacturing process, in which cleaning liquid will enter the gap and flush the gap at the same time. In view of this, as shown in FIG. 16 and FIG. 17, the first tube body 11 of this embodiment includes a first section 11*a* surrounding the outside of the second tube body 12 and a second section 11*b* connected to a distal end of the first section 11*a*. The first section 11*a* is provided with a notch 11*a*1. The sleeved stainless-steel tube and helical tube can be fully flushed through the notch 11*a*1, and flushing liquid can easily flow out of the notch after the cleaning process, thus avoiding the cleaning liquid remaining in the gap. At the same time, the hardness of a sleeving section between the first tube body 11 and the second tube body 12 is transitioned to avoid high local hardness, whereby the compliance of the sheath core 10 is better. It should be noted that the distal end of the first section 11*a* is closed so that the end has a closed section by which the distal ends of the first tube body 11 and the second tube body 12 can be welded.

Preferably, multiple notches 11*a*1 are provided at intervals along an axial direction of the first section 11*a*, and the entire sleeving section can be fully cleaned by the multiple notches 11*a*1 in the axial direction while the hardness of the entire section is transitioned. As an embodiment, the adjacent notches 11*a*1 on the first section 11*a* are provided at equal intervals from a proximal end of the first section 11*a* to the distal end thereof. As another embodiment, the adjacent notches 11*a*1 on the first section 11*a* are provided at gradually reducing intervals from a proximal end of the first section 11*a* to the distal end thereof. The distance between the proximal and distal notches 11*a*1 is gradually reduced, whereby the adjacent notches 11*a*1 are gradually increased from the proximal end to the distal end, and the hardness transition from the proximal end to the distal end is better, and the flexibility towards the distal end is better.

With continued reference to FIG. 16 and FIG. 17, in other embodiments, the notch 11*a*1 is a helical notch which extends helically along an axial direction of the first section 11*a* in order to facilitate the cleaning of the gap within the entire sleeving section at the same time as machining. Preferably, as an embodiment, the adjacent notches 11*a*1 on the first section 11*a* are provided at equal intervals W from a proximal end of the first section 11*a* to the distal end thereof. As another embodiment, the adjacent notches 11*a*1 on the first section 11*a* are provided at gradually reducing intervals W from a proximal end of the first section 11*a* to the distal end thereof, whereby the adjacent notches 11*a*1 are gradually increased from the proximal end to the distal end, and the transition from the proximal end to the distal end is better, and the flexibility towards the distal end is better.

In the sleeving process, preferably, as shown in FIG. 16, the length L5 between the distal and the proximal notches 11*a*1 on the first section 11*a* of this embodiment is 5-200 mm. This length orientation ensures as much as possible the compliance of the transition section and the rigidity of other sections of the sheath core 10, whereby the main body of the sheath core 10 has sufficient pushing property.

In this embodiment, the sheath core 10 is designed by combining a helical tube and a stainless-steel tube. The stainless-steel tube wraps an outer wall of the helical tube. The sheath core adopts the structure where the helical tube is located at a distal end while the stainless-steel tube is located at a proximal end. A notch is provided at a distal end of the stainless-steel tube, and the distal end is a closed section for being welded and fixed to the helical tube and sealing the notch. The notch achieves a flexible even transition between the helical tube and the stainless-steel tube, ensures the flexibility of the distal end of the sheath core 10 and the rigidity of the proximal end, and ensures that a main body of the sheath core 10 has sufficient pushing property. The sheath core assembly 100 of this embodiment solves the problem of difficulty in pushing and withdrawing caused by the poor compliance of the distal end of the existing sheath core 10.

Embodiment 4

Referring to FIG. 7, FIG. 10, and FIG. 15, on the basis of Embodiments 1 and 2, this embodiment further provides a sheath core assembly 100. The sheath core assembly 100 of this embodiment includes a sheath core 10, a U-shaped anchor 20 surrounding the sheath core 10 and relatively fixed to the sheath core 10, a connector 30 surrounding the distal end of the sheath core 10 and configured to connect the sheath core 10 to a tip 40, and the tip 40 wrapping the distal end of the sheath core 10. The specific structure of the U-shaped anchor 20 in this embodiment refers to Embodiment 1 and will not be described herein. The specific structure of the connector 30 in this embodiment refers to Embodiment 2 and will not be described herein. The specific structure of the sheath core 10 in this embodiment refers to Embodiment 3 and will not be described herein.

In this embodiment, the sheath core 10 is designed by combining a helical tube and a stainless-steel tube. The stainless-steel tube wraps an outer wall of the helical tube. The sheath core adopts the structure where the helical tube is located at a distal end while the stainless-steel tube is located at a proximal end. A notch is provided at a distal end of the stainless-steel tube, and the distal end is a closed section for being welded and fixed to the helical tube and sealing the notch. The notch achieves a flexible even transition between the helical tube and the stainless-steel tube, ensures the flexibility of the distal end of the sheath core 10 and the rigidity of the proximal end, and ensures that a main body of the sheath core 10 has sufficient pushing property. The sheath core assembly 100 of this embodiment not only solves the problem of difficulty in withdrawing caused by the steps in the welding zone, but also solves the problems of difficulty in pushing and withdrawing and fracture failure caused by the existing bifurcation tube and the problem of difficulty in pushing and withdrawing caused by the poor compliance of the distal end of the existing sheath core 10.

Embodiment 5

This embodiment provides a delivery instrument. The delivery instrument includes any sheath core assembly 100 in Embodiment 1 to Embodiment 4.

The present invention provides a sheath core assembly and a delivery instrument including the sheath core assembly. An outer periphery of an anchor body is arranged as an arc-shaped transition face, and a welding groove is recessed in the arc-shaped transition face, whereby a distal end of the anchor body has no step, thus solving the problem of difficulty in pushing and withdrawing due to the existence of steps in a welding zone, and greatly improving the smoothness of withdrawal of a delivery device in blood vessels, especially curved blood vessels. In addition, built-in welding spots avoid damage to the blood vessels by surface unevenness caused by welding, thus further improving the smoothness.

The present invention provides a sheath core assembly and a delivery instrument including the sheath core assembly. By designing a welding zone and a circumferential fixing zone of a connector in the same groove, the overall length of the connector is obviously smaller than the length of the existing bifurcation tube. By reducing the overall length, after the connector is buried in a tip, the length of a high-hardness zone of the tip is smaller, and the compliance is better. At the same time, the overall structure of the connector is more stable, and the connector will not be deformed during injection molding of the tip and is more reliably connected to the tip, thus solving the problems of difficulty in pushing and withdrawing and the fracture failure caused by the existing bifurcation tube.

The present invention provides a sheath core assembly and a delivery instrument including the sheath core assembly. A sheath core 10 is designed by combining a helical tube and a stainless-steel tube. The stainless-steel tube wraps an outer wall of the helical tube. The sheath core adopts the structure where the helical tube is located at a distal end while the stainless-steel tube is located at a proximal end. A notch is provided at a distal end of the stainless-steel tube, and the distal end is a closed section for being welded and fixed to the helical tube and sealing the notch. The notch achieves a flexible even transition between the helical tube and the stainless-steel tube, ensures the flexibility of the distal end of the sheath core 10 and the rigidity of the proximal end, ensures that a main body of the sheath core 10 has sufficient pushing property, and solves the problem of difficulty in pushing and withdrawing caused by the poor compliance of the distal end of the existing sheath core.

The various technical features of the above embodiments may be combined randomly. In order to simplify the description, all possible combinations of the various technical features in the above-mentioned embodiments are not described. However, as long as the combinations of these technical features do not contradict, the combinations should be considered to be the scope of the description.

The above-mentioned embodiments express only a few implementations of the present invention, which are described in greater detail but are not to be construed as limiting the scope of the present invention. It will be appreciated by those of ordinary skill in the art that numerous variations and modifications may be made to the present invention without departing from the concept of the present invention, which fall within the protection scope of the present invention. Therefore, the protection scope of the present invention should be determined by the appended claims.

The invention claimed is:

1. A sheath core assembly, comprising a sheath core and a U-shaped anchor, wherein the U-shaped anchor comprises an anchor body and a stent fixing rod; the anchor body surrounds the sheath core and is relatively fixed to the sheath core; the anchor body comprises a distal face and a proximal face which are opposite to each other, and an outer peripheral face surrounded between the distal face and the proximal face; the distal face is larger than the proximal face, and wherein edges of the distal face and the proximal face are arc-shaped; the outer peripheral face is an arc face having a smooth transition from the distal face to the proximal face; and a proximal end of the stent fixing rod is fixedly connected to the distal face of the anchor body; wherein the anchor body is axially provided with two symmetrical pulling wire holes, and the pulling wire holes are opposite to exhaust grooves on a tip in the sheath core assembly.

2. The sheath core assembly according to claim 1, wherein the distal face and the proximal face have the same shape.

3. The sheath core assembly according to claim 2, wherein both the distal face and the proximal face of the anchor body are round, whereby the anchor body is approximately conical.

4. The sheath core assembly according to claim 3, wherein an accommodating groove cut from the distal face is recessed in the outer peripheral face near a distal end of the anchor body, and the accommodating groove is provided near the stent fixing rod, whereby a connecting arm of a stent hooked on the stent fixing rod is placed in the accommodating groove.

5. The sheath core assembly according to claim 2, wherein both the distal face and the proximal face of the anchor body are elliptic, whereby the anchor body is approximately elliptically conical.

6. The sheath core assembly according to claim 1, wherein a welding groove is recessed in the outer peripheral face near the proximal end of the anchor body.

7. The sheath core assembly according to claim 1, further comprising a connector surrounding a distal end of the sheath core and configured to connect the sheath core to a tip in the sheath core assembly, wherein a groove is recessed in an outer peripheral surface of the connector, and the connector is relatively fixed to the sheath core and the tip through the groove.

8. The sheath core assembly according to claim 7, wherein the connector has a polygonal radial cross-section, whereby an outer peripheral face of the connector comprises multiple surfaces, and the groove is recessed in the outer peripheral surface of the connector.

9. The sheath core assembly according to claim 7, wherein the connector has a quadrilateral radial cross-section, whereby the outer peripheral face of the connector comprises four surfaces, and the groove comprises a first groove provided on the surface and cut from a distal face and a proximal face of the connector and/or comprises a second groove recessed circumferentially along the outer peripheral face of the connector.

10. The sheath core assembly according to claim 1, wherein the sheath core comprises a first tube body and a second tube body retained in the first tube body, a distal end of the second tube body extends out of a distal face of the first tube body, and the compliance of the second tube body is superior to that of the first tube body.

11. The sheath core assembly according to claim 10, wherein the first tube body is a cylindrical tube, and the second tube body is a helical tube.

12. A sheath core assembly, comprising a sheath core and a U-shaped anchor, wherein the U-shaped anchor comprises an anchor body and a stent fixing rod; the anchor body surrounds the sheath core and is relatively fixed to the sheath core; the anchor body comprises a distal face and a proximal face which are opposite to each other, and an outer peripheral face surrounded between the distal face and the proximal face; the distal face is larger than the proximal face, and wherein the edges of the distal face and the proximal face are arc-shaped; the outer peripheral face is an arc face having a smooth transition from the distal face to the proximal face; and a proximal end of the stent fixing rod is fixedly connected to the distal face of the anchor body;

further comprising a connector surrounding a distal end of the sheath core and configured to connect the sheath core to a tip in the sheath core assembly, wherein a groove is recessed in an outer peripheral surface of the connector;

wherein the groove recessed circumferentially along the outer peripheral face of the connector, blocking portions are formed at a proximal side and a distal side of the groove respectively and have quadrilateral radial cross-sections, and two opposite sides of the quadrilateral are straight lines while the other two opposite sides are arc lines, whereby two opposite faces of the blocking portion are arc faces, and the arc faces of the two blocking portions at the proximal side and the distal side are interlaced in azimuth.

13. A sheath core assembly, comprising a sheath core and a U-shaped anchor, wherein the U-shaped anchor comprises an anchor body and a stent fixing rod; the anchor body surrounds the sheath core and is relatively fixed to the sheath core; the anchor body comprises a distal face and a proximal face which are opposite to each other, and an outer peripheral face surrounded between the distal face and the proximal face; the distal face is larger than the proximal face, and wherein the edges of the distal face and the proximal face are arc-shaped; the outer peripheral face is an arc face having a smooth transition from the distal face to the proximal face; and a proximal end of the stent fixing rod is fixedly connected to the distal face of the anchor body:

wherein the sheath core comprises a first tube body and a second tube body retained in the first tube body, a distal end of the second tube body extends out of a distal face of the first tube body, and the compliance of the second tube body is superior to that of the first tube body;

wherein the first tube body is a cylindrical tube, and the second tube body is a helical tube;

wherein the first tube body comprises a first section surrounding the outside of the second tube body and a second section connected to a proximal end of the first section, and the first section is provided with a notch, wherein multiple notches are provided at intervals along an axial direction of the first section.

14. The sheath core assembly according to claim 13, wherein the adjacent notches on the first section are provided at equal intervals from a proximal end of the first section to the distal end thereof.

15. The sheath core assembly according to claim 13, wherein the adjacent notches on the first section are provided at gradually reducing intervals from a proximal end of the first section to the distal end thereof.

16. The sheath core assembly according to claim 13, wherein the notch is a helical notch which extends helically along an axial direction of the first section.

17. The sheath core assembly according to claim 16, wherein the adjacent helical notches on the first section are provided at gradually reducing intervals from a proximal end of the first section to the distal end thereof.

18. The sheath core assembly according to claim 13, wherein the length between the nearest and farthest notches on the first section is 5-200 mm.

* * * * *